United States Patent [19]

Shoji et al.

[11] Patent Number: 5,231,105
[45] Date of Patent: Jul. 27, 1993

[54] ETHYLAMINE DERIVATIVES AND ANTIHYPERTENSIVES CONTAINING THE SAME

[75] Inventors: Masataka Shoji; Kozo Toyota; Chikahiko Eguchi; Ryota Yoshimoto; Yosikatsu Koyama; Hideki Domoto; Akira Kamimura, all of Kawasaki, Japan

[73] Assignee: Ajinomoto Co., Inc., Tokyo, Japan

[21] Appl. No.: 354,880

[22] Filed: May 22, 1989

Related U.S. Application Data

[63] Continuation-in-part of Ser. No. 201,911, Jun. 2, 1988, abandoned.

[30] Foreign Application Priority Data

Jun. 2, 1987 [JP] Japan ................. 62-138405
Nov. 18, 1988 [JP] Japan ................. 63-293408
Nov. 30, 1988 [JP] Japan ................. 63-303461

[51] Int. Cl.$^5$ ............... C07D 211/70; C07D 211/34; A61K 51/445
[52] U.S. Cl. .................. 514/325; 514/317; 514/318; 514/326; 514/327; 514/330; 514/331; 514/212; 514/213; 546/207; 546/208; 546/212; 546/243; 546/214; 546/215; 546/216; 546/225; 546/230; 546/232; 546/233; 546/237; 546/240
[58] Field of Search ............... 546/203, 204, 208, 212, 546/213, 214, 215, 216, 225, 230, 232, 233, 237, 240; 514/325, 317, 318, 326, 327, 330, 331

[56] References Cited

U.S. PATENT DOCUMENTS

| | | | |
|---|---|---|---|
| 3,759,928 | 9/1973 | Zivkovic | 546/232 |
| 3,806,526 | 4/1974 | Carr et al. | 546/237 |
| 3,878,217 | 4/1975 | Carr et al. | 546/240 |
| 4,031,222 | 6/1977 | Remy | 546/203 |
| 4,254,130 | 3/1981 | Carr et al. | 546/237 |
| 4,285,957 | 8/1981 | Carr et al. | 546/240 |
| 4,285,958 | 8/1981 | Carr et al. | 546/240 |
| 4,912,222 | 3/1990 | Griffith et al. | 546/203 |

FOREIGN PATENT DOCUMENTS 1242162 8/1971 United Kingdom ............... 546/232

Primary Examiner—Robert T. Bond
Attorney, Agent, or Firm—Oblon, Spivak, McClelland, Maier & Neustadt

[57] ABSTRACT

An ethylamine derivative of formula (I):

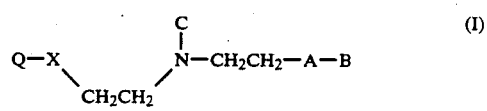

wherein
A represents a carbon atom or a nitrogen atom;
B represents a substituted or unsubstituted aralkyl or aryl group;
C represents hydrogen, alkyl, aralkyl, or aryl, each of which may optionally be substituted or
C may optionally be bonded to A to form an alkylene bridge which is optionally substituted,
Q represents a substituted or unsubstituted aryl group, said group optionally being substituted by hetero atom(s) or substituent(s) optionally containing hetero atom(s); and
X represents an alkylene bridge having from 2 to 20 carbon atoms and is optionally substituted with groups which include hetero atoms with the non-hetero atom substituents optionally containing hetero atoms.

23 Claims, No Drawings

ETHYLAMINE DERIVATIVES AND ANTIHYPERTENSIVES CONTAINING THE SAME

CROSS-REFERENCE TO RELATED APPLICATIONS

This application is a continuation-in-part of application Ser. No. 07/201,911 filed Jun. 2, 1988 now abandoned.

BACKGROUND OF THE INVENTION

1. Field of the Invention

The present invention relates to an ethylamine derivative, which exhibits antihypertensive properties.

2. Description of the Background

It is said that there are about 13,000,000 hypertension patients in Japan, and the frequency of hypertension is higher with advancement in age. In addition, the condition of hypertension is an important factor in cerebral apoplexy and cardiopathy which are the second and third highest causes of death, respectively. Accordingly, antihypertensive drugs are one of the most important classes of drugs in the treatment of gereatric diseases.

About 90% or more of hypertensive patients are believed to suffer from essential hypertension, the cause of which is not clear, and the remedy therefore is merely within the range of an expectant treatment for the disease. Accordingly, patients are required to continuously take an antihypertensive drug all of their lives, and so the antihypertensive drug should have high safety and a sure pharmaceutical activity against hypertensive and further must be durable.

Recently, the serotonin-antagonistic antihypertensives have been reported. However, these compounds are not always satisfactory from the viewpoint of their antihypertensive mechanism, as well as their durability. In addition, serotonin-antagonistic drugs have been reported to be effective against various diseases caused by serotonin, for example, thrombosis, ulcers and the like, but the effect of such drugs against such diseases is not so clear. On the other hand, from the viewpoint of the preparation of the said antihypertensives, not an insignificant number of compounds and synthetic intermediates for the antihypertensives are difficultly soluble in organic solvents or are produced by procedures which are complicated and troublesome. A need therefore continues to exist for antihypertensive drugs which can be conveniently prepared at low cost and which have excellent overall effective properties.

SUMMARY OF THE INVENTION

Briefly, one object of the present invention is to provide an antihypertensive drug which has several desirable features in its stated function and which is conveniently able to be produced industrially.

Accordingly, this object and other objects of the present invention as hereinafter will become more readily apparent can be attained by an ethylamine derivative of formula (I):

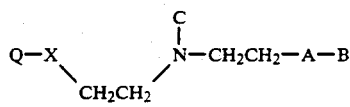

(I)

wherein

A represents a carbon atom or a nitrogen atom;

B represents a substituted or unsubstituted aralkyl or aryl group;

C represents hydrogen, alkyl, aralkyl, or aryl, each of which may optionally be substituted or C may optionally be bonded to A to form an alkylene bridge which is optionally substituted, Q represents a substituted or unsubstituted aryl group, said group optionally being substituted by hetero atom(s) or substituent(s) optionally containing hetero atom(s); and X represents an alkylene bridge having from 2 to 20 carbon atoms and is optionally substituted with groups which include hetero atoms with the non-hetero atom substituents optionally containing hetero atoms.

DETAILED DESCRIPTION OF THE PREFERRED EMBODIMENTS

In the structure of the compound above, the radical Q includes the likes of

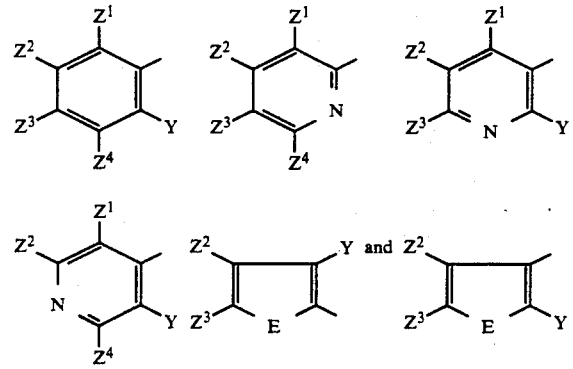

in which

E represents a nitrogen atom, substituted nitrogen, an oxygen atom or a sulfur atom;

Y, $Z^1$, $Z^2$, $Z^3$ and $Z^4$ may be same or different and each represents a hydrogen atom or a substituted or unsubstituted alkyl, aralkyl or aryl group, and a part of the organic groups may optionally be substituted by hetero atom(s) or substituent(s) optionally containing hetero atom(s); Y may optionally be bonded to X to form an alkylene bridge or an alkylene bridge having at least one oxygen, sulfur or nitrogen atom and optionally having substituent(s); and $Z^1$ and $Z^2$, $Z^2$ and $Z^3$, or $Z^3$ and $Z^4$ may optionally be bonded to each other to form an alkylene bridge or an alkylene bridge having at least one oxygen, sulfur or nitrogen atom and optionally having substituent(s).

In the structure of the present compound, radical B represents an aralkyl group or an aryl group having for 6 to 16 carbon atoms which is optionally substituted.

C represents a hydrogen atom or an alkyl group having from 1 to 6 carbon atoms which is optionally substituted. C may be optionally bonded to A to form an alkylene bridge having 1 to 6 carbon atoms and is optionally substituted. Other suitable groups for radical C include hydrogen, methyl, ethyl, propyl, butyl, pentyl and hexyl. Further, C may be bonded to A as a methylene, ethylene or propylene group.

Structural examples of the unit A-B in the formula include:

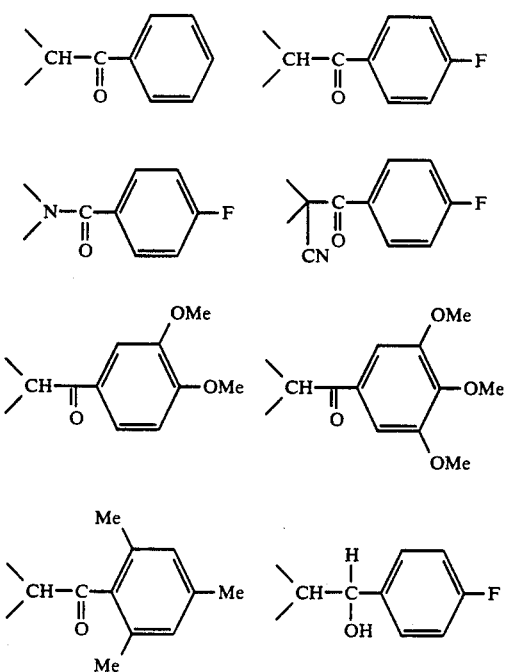
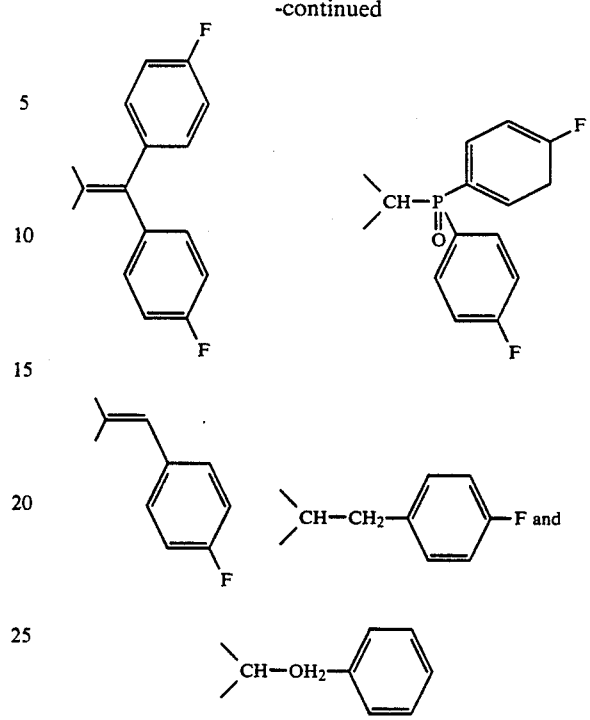
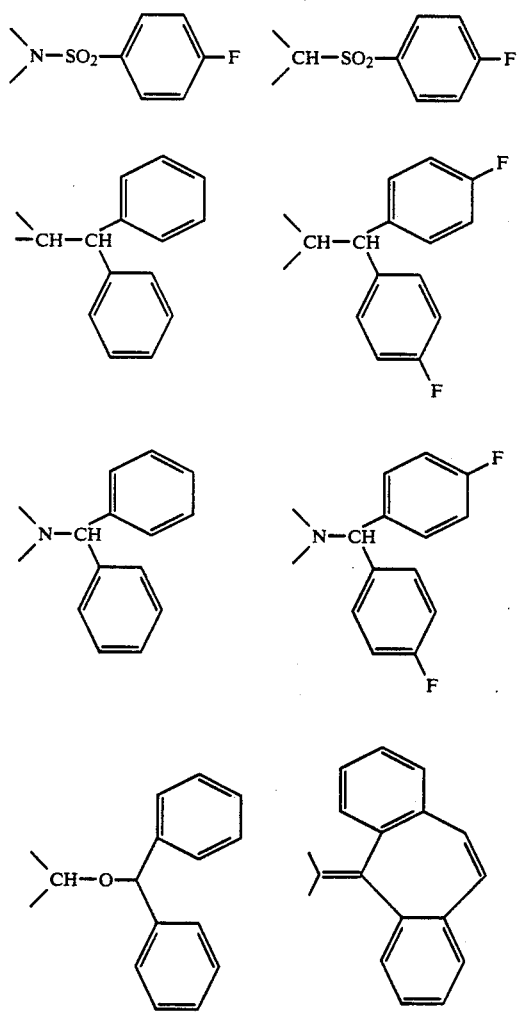

In the formulas II to III above, Y, $Z^1$, $Z^2$, $Z^3$ and $Z^4$ may be same or different and each represents a hydrogen atom or a lower alkyl group having from 1 to 6 carbon atoms, an aralkyl group having 6 to 12 carbon atoms or an aryl group having from 6 to 12 carbon atoms, each of which is optionally substituted, or the organic groups are each substituted by halogen atom(s) and/or at least one oxygen atom, sulfur atom, nitrogen atom or phosphorus atom. More preferably, Y, $Z^1$, $Z^2$, $Z^3$ and $Z^4$ may be same or different and each represents a hydrogen atom, a halogen atom, a hydroxyl group, an amino group, a hydroxyamino group, a nitro group, or a cyano group, or an organic group selected from the group consisting of an alkyl group, an aralkyl group, an aryl group, an alkoxy group, an aralkyloxy group, an aryloxy group, an alkylamino group, an aralkylamino group, an arylamino group, an acylamino group, an acyloxy group and an aminosulfonyl group, each of which may be substituted.

Suitable examples of radical Q in formula I above include: o-nitrophenyl, o-aminophenyl, o-ethylcarbamoylphenyl, o-styrylcarbamoylphenyl, 1-naphthyl, 2-naphthyl, 3,4-dimethoxyphenyl, 3,4,5-trimethoxyphenyl, 3,4-dichlorophenyl, 3-methoxyphenyl, 3,4-dihydroxyphenyl 3-trifluoromethylphenyl, pyrrolyl, N-methylpyrrolyl, 4-methoxyphenyl, 3-benzoylphenyl, phenyl, 3,4-dimethylphenyl, 2-methoxy-5·bromophenyl, 2-fluorophenyl, 3-fluorophenyl, 3-fluoro-4-methoxyphenyl, 3-chlorophenyl, 3-iodophenyl, 3-phenoxyphenyl, 3-methoxy-4-benzyloxyphenyl, 3,5-dimethoxyphenyl, 3-benzyloxyphenyl, 3,4-dibenzyloxyphenyl, 3-ethoxy-4-methoxyphenyl, 3-ethoxyphenyl, 2-methylnaphthyl, 2-bromophenyl, 2-bromo-4,5-dimethoxyphenyl, pentafluorophenyl, 2-chlorophenyl, 2,3,6-trichlorophenyl, 2,4-dichlorophenyl, 2-chloro-6 fluorophenyl, 2,6-dichlorophenyl, 2-6-dimethylphenyl, 2-iodophenyl, 2-nitro-4-trifluoromethylphenyl, 2-phenoxyphenyl, 2-methoxyphenyl, 2,3-dimethoxyphenyl, 2,3,4-trimethoxyphenyl, 2,4,5-trimethoxyphenyl, 2,5- dimethoxyphenyl, 2-benzyloxyphenyl, 2-ethoxyphenyl, 0-biphenyl, 2-trifluorophenyl, 2-methylphenyl, 2,3-dimethyl-4-methoxyphenyl, 3-methylphenyl, 3-methyl-4-methoxyphenyl, 3,4-dimethylphenyl, 3,4,5-trimethylphenyl, 4-cyanophenyl, 4-bromophenyl, 4-fluorophenyl, 4-chlorophenyl, 4-iodophenyl, 4-phenoxyphenyl, 4-benzyloxyphenyl, 4-ethoxyphenyl, 3-methoxy- 4-ethoxyphenyl, 4-(2-diethylaminoethoxy)phenyl, 3-methoxy-4-hydroxy-5-bromophenyl, 3-methoxy-4-hydroxyphenyl, 3,5-dimethoxy-4-hydroxyphenyl, 3-ethoxy-4-hydroxyphenyl, p-biphenyl, 4-butoxyphenyl, 4-(2-methyl-2-butyl)phenyl, 4-isopropylphenyl, p-tolyl, 4-benzylphenyl, 4-ethylphenyl, 4-hydroxyphenyl, 2-cyano-4-methylphenyl, 3,4-methylenedioxyphenyl, 3-pyridyl, 2-nitrophenyl, 2-chloro-4-nitrophenyl, 3-nitrophenyl, 2-nitro-5-fluorophenyl, 4-nitrophenyl, 4-aminophenyl, 3,5-di(trifluoromethyl)phenyl, 2,4-difluorophenyl, 2,5-difluorophenyl, 2,6-difluorophenyl, 3,4-difluorophenyl, 2,4-di(trifluoromethyl)phenyl, 3,5-difluorophenyl, 4-ethenylphenyl, 2,4,5-trimethylphenyl, 2-hydroxy-3-methoxyphenyl, 2-hydroxy-3-ethoxyphenyl, 4-(2-methylpropyl)phenyl, 4-methoxycarbonylphenyl, 3,4-diethoxyphenyl, 2-iodo-4,5-dimethoxyphenyl, 4-neopentanoylphenyl, 2-nitro -4,5-dimethoxyphenyl, 2-thiopheno, 2-furyl, 3-pyrrolyl, N-methyl-3-pyrrolyl, 3-thiopheno, 3-furyl and the like.

In the structure of formula I, group X preferably is

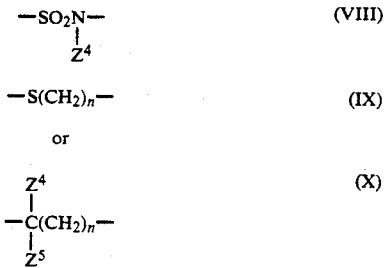

in which n represents an integer from 0 to 9; $Z^4$ and $Z^5$ are the same or different and each represents a hydrogen atom, an alkyl group, an aralkyl group, each of which is optionally substituted; and the organic groups may be optionally substituted by hetero atom(s) or substituents optionally containing hetero atom(s).

More preferably, group X is:

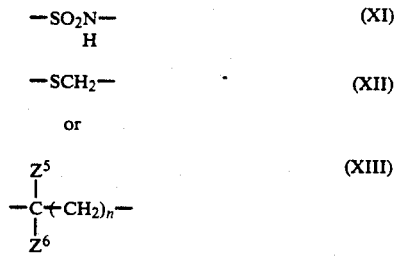

in which n represents a value from 0 to 9; $Z^5$ and $Z^6$ each represent an alkyl group having from 1 to 20 carbon atoms which is optionally substituted, and the organic groups may be optionally substituted by hetero atom(s) or substituent(s) optionally containing hetero atom(s).

The ethylamine derivative of the present invention may be in the form of a salt thereof.

Of course, when the salt of the same derivative is the active antihypertensive ingredient of a formulation, it is required to be in the form of a pharmaceutically acceptable salt of the derivative.

The ethylamine derivative of the present invention can be advantageously used as an antihypertensive in the treatment of hypertensive mammals and humans. The present compound can be perorally administered in the form of a preparation such as a tablet, a capsule or an elixir, or it may be parenterally administered in the form of a sterile solvent solution or suspension, for the purpose of blood pressure depression. The ethylamine derivative of the present invention can be administered to patients or animals which must be treated with an antihypertensive agent several times each in unit dosages of from 0.2 to 500 mg/patient or animal, and accordingly, the total dosage of the derivative may range from 1 to 2000 mg/patient or animal/day. It is a matter of course that the dosage required to achieve necessary and essential treatment may be varied in accordance with the condition of the disease, the weight of the patient or animal and other factors which are considered necessary by one skilled in the art.

The ethylamine derivative of the present invention can also be used together with any other antihypertensive agent. Suitable examples of the antihypertensive agents which can be used together with the derivative of the present invention include an $\alpha_1$-antagonist such as prazosin or the like; a calcium-antagonist such as nifedipine, nicardipine, diliagen, verapanil and the like; and a convertase inhibitor such as captopril emalopril, and the like.

A typical antihypertensive composition within the scope of the present invention contains from about 0.2 to about 500 mg of the derivative of the present invention or a physiologically acceptable salt thereof or a mixture thereof blended with a physiologically acceptable vehicle, carrier, extender, binder, antiseptic, stabilizer, flavoring agent or the like in a unit amount as required for a conventional pharmaceutical preparation. The amount of the active ingredient in the pharmaceutical composition or preparation should be such that an appropriate dosage falling within the indicated range can be obtained by the administration of the said composition or preparation.

Examples of pharmaceutical excipients which are combined with the present antihypertensive agent for the preparation of tablets, capsules and the like include binders such as tragacanth, gum arabic, corn starch or gelatin; a vehicle such as fine crystalline cellulose; an extender such as corn starch, pre-gelatinated starch, alginic acid, or the like; a sweetener such as sucrose, lactose or saccharin; a flavoring agent such as peppermint, an oil from Gaulthenia adenothrix Maxim or cherry. When the unit preparation is in the form of a capsule, the composition may further contain a liquid carrier such as a fat or oil, in addition to the above-mentioned additive materials. Other ingredients may be employed which form coated pills or which vary the physical form of the unit preparation by a different method. For example, tablets can be coated with shellac, sugar or a combination thereof. A syrup or elixir can contain the active compound together with sucrose as a sweetener, methyl- or propyl-paraben as an antiseptic, a dye and cherry or orange aroma as a flavoring agent.

A sterile composition for injection can be prepared in a conventional manner, for example, by dissolving or suspending the active substance in a vehicle such as distilled water for injection, together with a natural vegetable oil such as sesame oil, coconut oil, peanut oil, cotton seed oil or the like or a synthetic fat vehicle such as ethyl oleate or the like. If desired, a buffer, an antiseptic, an antioxidant or the like can be incorporated into the composition.

Having now fully described the invention, it will be apparent to one of ordinary skill in the art that many changes and modifications can be made thereto without departing from the spirit or scope of the invention as set forth herein.

EXAMPLES

Example 1: Synthesis of 1-[2-(2-nitrobenzenesulfonyl)aminoethyl]-4-(4-fluorobenzoyl)piperidine (a) Synthesis of (2-nitrobenzenesulfonyl)aminoethyl bromide A 20 ml amount of a dichloroethane solution of 21.0 g (200 mmol) of triethylamine was added dropwise to 80 ml of a dichloroethane solution containing 22.1 g (100 mmol) of 2-nitrobenzenesulfonyl chloride and 20.4 g (100 mmol) of 2-bromoethylamine hydrobromide, while cooled with ice. After the completion of the dropwise addition, the mixture was stirred overnight at room temperature. After the reaction, the reaction mixture was washed twice with 100 ml of 1N hydrochloric acid solution and then once with 100 ml of water, and then the organic layer was dried with anhydrous sodium sulfate.

The solvent was evaporated under reduced pressure and the above-entitled compound was obtained in the form of crystals.

Yield: 29.5 g (95.4 mmol), 95%.
Thin Layer Chromatography: (TLC) (AcOEt:n—$C_6H_{14}=1:4$).
$R_f=0.70$.
Mass Spectrum: MS (FAB, m/z) 309 ($M+H^+$).
Nuclear Magnetic Resonance Spectrum ($^1$H-NMR): (TMS/CDCl$_3$, δ/ppm) 3.45~3.65 (4H, m), 6.75 (1H, z), 7.53~8.08 (4H, m).

(b) Synthesis of 1-[2-(2-nitrobenzenesulfonyl)aminoethyl]-4-(4-fluorobenzoyl)piperidine)

A mixture comprising 9.27 g (30 mmol) of (2-nitrobenzenesulfonyl)aminoethyl bromide, 7.31 g (30 mmol) of 4-fluorobenzoylpiperidine hydrochloride, 8.48 g (80 mmol) of sodium carbonate and 100 ml of methyl isobutyl ketone was stirred overnight in an oil bath.

After the reaction, 50 ml of water was added to the reaction mixture for washing, and then the organic layer was isolated and the solvent was evaporated under reduced pressure.

After purification by silica gel column chromatography (eluent: chloroform/methanol=5/1), the resulting product was converted into its hydrochloride with 4N hydrogen chloride/dioxane solution.

Yield: 10.5 g (22.2 mmol), 76%.
TLC (CHCl$_3$:MeOH=9:1).
$R_f=0.81$.
MS (FAB, m/z) 436 ($M+H^+$).
$^1$H-NMR (TMS/DMSO-d$_6$, δ/ppm) 1.80~2.05 (5H, m), 3.04~3.35 (6H, m), 3.56~3.65 (2H, m), 3.65~3.75 (1H, m), 7.90~7.96 (2H, m), 7.40 (2H, dd, J=8, 8Hz), 8.45 (1H, bs), 8.02~8.13 (4H, m).

Example 2 Synthesis of 1-[2-(2-aminobenzenesulfonyl)aminoethyl]-4-(4-fluorobenzoyl)piperidine A suspension of 1-[2-(2-nitrobenzenesulfonyl)aminoethyl]-4-(4-fluorobenzoyl)piperidine (see Example 1) in 160 ml of acetic acid was heated at 90° C. and then 8 g of iron (powder) was gradually added thereto over a period of 10 minutes. The reaction solution became black, and then the solution was stirred for a further 10 minutes. A white crystalline material precipitated from solution. After cooling, the reaction solution was filtered, and the residue was washed with methanol. The solvent was evaporated from the resulting filtrate, and 4N hydrogen chloride/dioxane solution was added to the residue. Thus the above-entitled compound was obtained in the form of a hydrochloride thereof.

Yield: 65.8 g (13.8 mmol), 91%.
TLC (CHCl$_3$; MeOH=5:1).
$R_f=0.40$.
MS (FAB, m/z) 406 ($M+H^+$).
$^1$H-NMR (TMS/DMSO-d$_6$, δ/ppm) 1.84~2.01 (5H, m), 3.02~3.20 (6H, m), 3.48~3.55 (2H, m), 3.64~3.72 (1H, m), 4.72~ (1H, bs), 6.63 (1H, dd, J=8, 8Hz), 6.84 (1H, dd, J=8Hz), 7.30 (1H, dd, J=8, 8Hz), 7.39 (2H, dd, J=6, 6Hz), 7.53 (1H, dd, J=8Hz), 7.98 (1H, bs), 8.08 (2H, dd, J=8, 6Hz).

Example 3: Synthesis of 1-[2-(2-ethoxycarbonylaminobenzenesulfonyl)aminoethyl]-4-(4-fluorobenzoyl)piperidine Thirty ml of a chloroform solution containing 3.65 g (9.00 mmol) of 1-[2-(2-aminobenzenesulfonyl)aminoethyl]-4-(4-fluorobenzoyl)piperidine, 0.16 g (0.90 mmol) of 4-piperidinopyridine and 0.91 g (9.00 mmol) of triethylamine was stirred and 0.976 g (9.00 mmol) of ethyl chloroformate was dropwise added thereto. After the completion of the reaction, the reaction mixture was stirred for 3 hours and then extracted twice with 50 ml of 1N hydrochloric acid and then once with 50 ml of water in the stated order. Next, the resulting organic layer was dried with anhydrous magnesium sulfate.

The solvent was evaporated and the residue was purified by column chromatography (eluent: ethyl acetate/ethanol=20/1). The above-entitled compound was obtained as an oily product.

Yield: 3.18 g (6.67 mmol), 74.1%.
TLC (AcOEt:EtOH=20:1).
$R_f=0.87$.
MS (D, m/I) 478 ($M+H^+$).
$^1$H-NMR (TMS/DMSO-d$_6$, δ/ppm) 1.12 (3H, t, J=8Hz), 1.82~2.10 (5H, m), 3.12~3.27 (2H, m), 3.65~3.77 (4H, m), 4.10 (2H, q, J=8Hz), 4.23~4.30 (2H, m), 6.16 (1H, bs), 6.68 (1H, dd, J=8, 8Hz), 6.89 (1H, d, J=8Hz), 7.36 (1H, dd, J=8.8Hz), 7.40 (2H, dd, (J=8, 6Hz), 7.59 (1H, d, J=8Hz), 8.10 (2H, dd, J=8, 6Hz).

Example 4: Synthesis of 5,6-benzo-2,4-diaza-2-[2-[(4-fluorobenzoyl)piperidin-1-yl]ethyl]tetrahydrothiopyrane-1,1-dioxide Twenty ml of a pyridine solution of 1.10 g (2.30 mmol) of 4-[2-(2-ethoxycarbonylaminobenzenesulfonyl)aminoethyl]-1-(4-fluorobenzoyl)piperidine (refer to Example 3) was heated at reflux for 15 hours. After the completion of the reaction, the solvent was evaporated, and dichloroethane-ether was added to the residue for crytallization. The resulting crystal was taken out by filtration, washed with ether and then dried under reduced pressure to obtain the above-entitled compound.

Yield: 0.31 g (0.72 mmol), 32%.
TLC (CHCl$_3$:MeOH=9:1).
R$_f$=0.66.
MS (FD, m/z) 432 (M+H$^+$).
$^1$H-NMR (TMS/CDCl$_3$, δ/ppm) 1.78~1.98 (5H, m), 2.38~2.52 (2H, m), 2.82~2.92 (2H, m), 3.05~3.14 (2H, m), 3.25 (1H, bs), 4.20 (2H, t, J=7Hz), 7.13 (2H, dd, J=8, 8Hz), 7.20 (1H, d, J=8Hz), 7.26 (1H, dd, J=8, 8Hz), 7.57 (1H, d, J=8, 8Hz), 7.80 (1H, d, J=8Hz), 7.94 (2H, dd, J=8, 8Hz).

Example 5 Synthesis of 2-[3,4-dimethoxyphenyl]-5-[4-(4-fluorobenzoyl)-1-piperidinyl]-2-isopropylvaleronitrile hydrochloride (a) Synthesis of 2-(3,4-dimethoxyphenyl)-2-isopropylacetonitrile A three-necked flask equipped with an argon balloon and two dropping funnels was flushed with argon and 6.6 g (90.17 mmol) of sodium amide was placed therein. After flushing again with argon, 30 ml of 1,2-dimethoxyethane was added thereto. A 25 g (0.14 mmol) amount of 3,4-dimethoxyphenylacetonitrile was placed in another flask, which was then added thereto. The solution was transferred into the above-mentioned dropping funnels with a cylinder. The 3,4-dimethoxyphenylacetonitrile solution was added dropwise to the sodium amide suspension with stirring while being cooled with ice. The ice cooling bath was removed and then the whole was stirred for another hour. Next, the ice cooling bath was again applied to the reaction solution and a 1,2-dimethoxyethane solution (17 ml) containing 17.4 ml (0.19 mmol) of isopropyl bromide was added dropwise thereto, and then the reaction solution was stirred overnight at room temperature. The reaction mixture was poured into ice water, extracted with ether and then washed with a 1N aqueous sodium hydroxide solution, water, an aqueous 5% citric acid solution and water in the stated order. The ether layer was dried with anhydrous magnesium sulfate and the solvent was evaporated under reduced pressure to obtain 29.11 g of an oily product. A small amount of ethanol was added thereto for crystallization, and the resulting crystalline material was recrystallized. (3,4-Dimethoxyphenyl)-2-isopropylacetonitrile was obtained accordingly.

Yield: 19.2 g (8.77 mmol), 63%)

(b) Synthesis of 5-chloro-2-(3,4-dimethoxyphenyl)-2-isopropylvaleronitrile

A 0.32 g (8.2 mmol) amount of sodium amide was placed in a three-necked flask flushed with argon, and after further argon flushing, 5 ml of 1,2-dimethoxyethane was added thereto. A 1.49 g (6.8 mmol) amount of 2-(3,4-dimethoxyphenyl)-2-isopropylacetonitrile was placed in another flask, which was also flushed with argon. Then 10 ml of 1,2-dimethoxyethane was added thereto. This solution was added dropwise to the above-prepared sodium amide suspension via a cylinder. After a while, the reaction mixture became cloudy white. The mixture was drawn into a cylinder and added dropwise to 1,2-dimethoxyethane (50 ml) containing 2.5 ml (26.3 mmol) of 1-bromo-3-chloropropane which had been prepared in another argon flushed flask. This mixture was stirred overnight at room temperature. Water was added to the reaction mixture, which was then extracted with chloroform and dried with anhydrous magnesium sulfate. Then the solvent was evaporated under reduced pressure to obtain 2.12 g of a crude product. The non-reacted starting materials were found to still remain in the reaction mixture by TLC (SiO$_2$/CHCl$_3$), but the reaction mixture was used in the next reaction as such without being further purified.

(c) Synthesis of 2-[3,4-dimethoxyphenyl]-5-[4-(4-fluorobenzoyl)1-piperidinyl]-2-isopropylvaleronitrile Fifty ml of toluene and 2.12 g of the above crude 5-chloro-2-(3,4-dimethoxyphenyl)-2-isopropylvaleronitrile were added to a mixture comprising 2.6 g (10.7 mmol) of 4-(4-fluorobenzoyl)piperidine hydrochloride and 0.9 g (8.5 mmol) of anhydrous sodium carbonate, and the mixture was heated at reflux. The reaction was traced by TLC and the heating was stopped at a pertinent step. Water was added to the reaction mixture, which was then extracted with chloroform. After drying over anhydrous magnesium sulfate, the solvent was evaporated under reduced pressure, and the crude product thus obtained was purified by silica gel column chromatography (CHCl$_3$/MeOH) to obtain the above-entitled compound.

Yield: 0.76 g (1.6 mmol). (0.2 g of the compound was converted into the hydrochloride).
TLC (CHCl$_3$:MeOH=9:1).
R$_f$=0.52.
MS (FD, m/z) 466 (M$^+$).
$^1$H-NMR (TMS/CDCl$_3$, δ/ppm) 0.80 (3H, d, J=7Hz), 1.20 (3H, d, J=7Hz), 1.9~3.5 (1.5H, m), 3.83 (3H, z), 3.88 (3H, z), 6.8–7.2 (5H, m), 7.8–8.1 (2H, m).

Example 6: Synthesis of 4-(4-fluorobenzoyl)-1-(4-phenylbutyl)piperidine hydrochloride (a) Synthesis of 4-phenylbutyl chloride A 2.2 ml (20 mmol) amount of thionyl chloride was added dropwise to a methylene chloride solution (30 ml) containing 3 g (20 mmol) of 4-phenyl-1-butanol and stirred overnight at room temperature. The reaction solution was washed with water, an aqueous 50% sodium hydrogen carbonate solution, water, 1N hydrochloric acid and water in that order, and then the solvent was dried with anhydrous magnesium sulfate. After distillation under reduced pressure, 3.62 g of a crude 4-phenylbutyl chloride was obtained. This material was used in the next reaction without being further purified.

(b) Synthesis of 4-(4-fluorobenzoyl)-1-(4-phenylbutyl)piperidine

A necessary amount of toluene, 1.8 g (12 mmol) of sodium iodide and 31 g of the crude phenylbutyl chloride were added to a mixture comprising 3 g (12.3 mmol) of 4-(4-fluorobenzoyl)piperidine hydrochloride and 2.6 g (24.5 mmol) of anhydrous sodium carbonate. The resulting mixture was heated at reflux. After reaction overnight, the heating was stopped. Water was added to the reaction mixture, which was then extracted with chloroform. The resulting extract was dried with anhydrous magnesium sulfate, and the solvent was evaporated under reduced pressure. The crude product thus obtained was purified by silica gel column chromatography to obtain the above-entitled compound.

Yield: 0.13 g (0.38 mmol), 3%.
TLC (CHCl$_3$:MeOH=5:1).
R$_f$=0.72.
MS (FD, m/z) 339 (M+).
$^1$H-NMR (TMS/CDCl$_3$, δ/ppm) 1.4–2.2 (10H, m), 2.2–2.7 (4H, m), 2.8–3.2 (3H, m), 6.9–7.2 (7H, m), 7.7–8.0 (2H, m).

Example 7: Synthesis of 1-[3-(2-cinnamoylaminophenylthio)propyl]-4-(4-fluorobenzoyl)piperidine (a) Synthesis of 1-chloro-3-(2-aminophenylthio)propane Twenty ml of an isopropyl alcohol solution of 6.25 g (50.0 mmol) of 2-aminothiophenol was added to 20 ml of an isopropyl alcohol solution containing 2.97 g (55.0 mmol) of sodium methoxide under a stream of nitrogen and the mixture was blended. After stirring for 30 minutes, the reaction mixture was cooled to 0° C. and successively 10 ml of a toluene solution of 1-bromo-3-chloropropane was added dropwise thereto. After completion of the addition, the mixture was stirred for 1 hour at room temperature and then heated under reflux for 1 hour for further reaction. Then 60 ml of 1N sodium hydroxide was added and the reaction mixture was extracted with 50 ml of ether. The solvent was evaporated to obtain a crude product of the above-entitled compound.

Yield: 9.52 g (47.2 mmol), 94%.
TLC (Et$_2$O).
R$_f$=0.85.
$^1$H-NMR (TMS/CDCl$_3$, δ/ppm) 1.83 (2H, tt, J=8, 8Hz), 2.80 (2H, t, J=8Hz), 3.57 (2H, t, J=8Hz), 4.20 (2E, bs), 6.50 (1H, dd, J=6.8 Hz), 6.62 (1H, d, J=8Hz), 7.05 (1H, dd, J=8, 8=Hz), 7.26 (1H, d, J=6Hz).

(b) Synthesis of 1-chloro-3-(2-cinnamoylaminophenylthio]propane

A ten ml amount of a dichloromethane solution of 3.33 g (20.0 mmol) of cinnamoyl chloride was added dropwise to 20 ml of a dichloromethane solution containing 4.02 g (20.0 mmol) of triethylamine at room temperature. After completion of the dropwise addition, the mixture was stirred overnight. After washing twice with 30 ml of 1N hydrochloric acid and then once with water in that order, the organic layer was dried with anhydrous magnesium sulfate. The solvent was evaporated and then the residue was recrystallized form dichloromethane-ether-hexane to obtain the above-entitled compound.

Yield 4.70 g (14.2 mmol), 71%.
TLC (Et$_2$O).
R$_f$=0.88.
$^1$H-NMR (TMS/CDCl$_3$, δ/ppm) 2.0 (2H, tt, J=8, 8Hz), 2.88 (2H, t, J=8Hz), 3.57 (2H, t, J=8Hz), 6.50 (1H, d, J=18Hz), 6.85–7.55 (9H, m), 7.65 (1H, d, J=18Hz), 8.55 (1H, bs).

(c) Synthesis of 1-[3-(2-cinnamoylaminophenylthio)propyl]-4-(4-fluorobenzoyl)piperidine Using 3.17 g (9.58 mmol) of 1-chloro-3-[2-(cinnamoylamino)phenylthio]propane, 2.33 g (9.58 mmol) of 4-(4-chlorobenzoyl)piperidine hydrochloride, 2.76 g (20.0 mmol) of potassium carbonate and 30 ml of isoamyl alcohol as starting materials, the same reaction as Example-1 was conducted. The product obtained was purified by column chromatography (eluent: chloroform/methanol=40/1) to obtain the above-entitled compound.

Yield: 2.97 g (6.10 mmol), 64%.
TLC (CHCl$_3$:MeOH=9:1).
R$_f$=0.51.
MS (FD, m/z) 502 (M+).
$^1$H-NMR (TMS/DMSO-d$_4$, δ/ppm) 1.30~2.02 (7H, m), 2.95~3.22 (3H, m), 7.10 (1H, d, J=8, 8Hz), 7.23 (1H, dd, J=8, 8Hz), 7.31 (1H, dd, J=8, 8Hz), 7.39 (1H, dd, J=9, 9Hz), 7.41 (2H, dd, J=8, 8Hz), 7.46 (1H, d, J=8Hz), 7.55 (1H, d, J=8Hz), 7.60 (2H, d, J=18Hz), 7.65 (2H, d, J=8Hz), 7.71 (1H, d, J=8Hz), 8.06 (2H, dd, J=8, 6Hz), 9.64 (1H, s).

Example 8: Synthesis of 1-[3-(2-aminophenylthio)1-propyl]-4-(4-fluorobenzoyl)-piperidine Using 3.73 g (18.5 mmol) of 1-chloro-3-(2-aminophenylthio)propane, 4.52 g (18.5 mmol) of 4-(4-fluorobenzoyl)-piperidine hydrochloride, 6.90 g (50.0 mmol) of potassium carbonate and 50 ml of butanol as starting materials, the same reaction as Example 1 was conducted. The product obtained was purified by silica gel chromatography (eluent: chloroform/methanol=40/1) to obtain the above-entitled compound.

Yield: 0.50 g (1.12 mmol) in the form of the dihydrochloride, 6%.
TLC (CHCl$_3$:MeOH=9:1).
R$_f$=0.66.
MS (FD, m/z) 373 (M+).
$^1$H-NMR (TMS/DMSO-d$_6$, δ/ppm) 1.80~2.04 (7H, m), 2.99 (2H, t, J=7Hz), 3.02~3.12 (2H, m), 3.20 (2H, t, J=8Hz), 3.52 (2H, d, J=12Hz), 4.56 (2H, bs), 7.00~7.12 (1H, m), 7.21~7.32 (2H, m), 7.39 (2H, dd, J=10, 10Hz), 7.55 (1H, d, J=8Hz), 8.10 (2H, dd, J=8, 8Hz).

Example 9 Synthesis of 4-(4-fluorobenzoyl)-1-(5-phenylpentyl)piperidine hydrochloride (a) Synthesis of 5-phenylpentyl bromide A 1.8 g (6.7 mmol) amount of phosphorus tribromide was added to a chloroform solution (20 ml) of 3.3 g (20 mmol) of 5-phenyl-1-pentanol and the resulting solution was heated at reflux for 4 hours. When the reaction was traced by TLC, the starting materials were found to still remain in the reaction mixture, and so 0.2 g of phosphorus tribromide was further added and heated at reflux. Afterwards, the reaction solution was washed with water and dried with anhydrous magnesium sulfate, and then the solvent was evaporated under reduced pressure. Thus, 4.30 g of a crude 5-phenylpentyl bromide was obtained.

(b) Synthesis of 4-(4-fluorobenzoyl)-1-(5-phenylpentyl)piperidine

Fifty ml of isopropyl alcohol and 2.26 g of the crude 5-phenylpentyl bromide were added to a mixture comprising 2.4 g (9.9 mmol) of 4-(4-fluorobenzoyl)piperidine hydrochloride and 2.1 g (19.8 mmol) of anhydrous sodium carbonate, and the resulting mixture was heated under reflux. The reaction was continued overnight and then the heating was stopped. The reaction mixture was concentrated under reduced pressure, and water was added thereto. This was extracted with chloroform. The resulting extract was dried with anhydrous magnesium sulfate and then the solvent was evaporated under reduced pressure. The crude product thus obtained was purified by silica gel column chromatography to obtain the above-entitled compound.

Yield: 2.18 g, 62%.
TLC (CHCl$_3$:MeOH=9:1).
R$_f$=0.41.
MS (FD, m/z) 353 (M+).

The compounds described in Experiments 10 to 108 below were synthesized by the same procedure described above.

Example 10

2-(3,4-Dimethoxyphenyl)-5-[4-(4-fluorobenzoyl)-1-piperidinyl]valeronitrile L-(+)-tartarate
TLC(CHCl$_3$:MeOH=9:1).
Rf=0.48.
MS(FD, m/z) 424(M+).
H-NMR(TMS/CDCl$_3$, δ/ppm) 1.8–2.4(8H,m), 2.9–3.7(6H,m), 3.85(3H,s), 3.88(3H,s), 3.8–4.4(2H,m), 6.8–6.9(3H,m), 7.1–7.2(2H,m), 7.9–8.0(2H,m).

Example 11

5-[4-(4-Fluorobenzoyl)-1-piperidinyl]-2-isopropyl-2-(3,4,5-trimethoxyphenyl)valeronitrile L-(+)-tartarate
TLC(CHCl$_3$:MeOH=9:1).
Rf=0.48.
MS(FD,m/z) 497(M+).
H-NMR(TMS/CDCl$_3$, δ/ppm) 0.76(3H,bs), 1.0–1.2(1H,m), 1.16(3H,bs), 1.4–2.5(12H,m), 2.9–3.4(3H,m), 3.82(3H,s), 3.87(3H,s), 6.6–6.8(2H,m), 6.6–6.8(2H,m), 7.0–7.2(2H,m), 7.8–8.1(2H,m), 7.0–7.2(2H,m).

Example 12

2-(3,4-Dimethoxyphenyl)-2-dodecyl-5-[4-(4-fluorobenzoyl)-1-piperidinyl]valeronitrile hydrochloride
TLC(CHCl$_3$:MeOH=9:1).
Rf=0.70.
MS(FD,m/z) (M+).
H-NMR (TMS/CDCl$_3$, δ/ppm) 0.84(3H,t,J=8Hz), 1.2–1.5(22H,m), 1.8–2.1(8H,m), 2.9–3.1(4H,m), 3.4–3.5(2H,m), 3.6–3.8(1H,m), 3.76(3H,s), 3.79(3H,s), 6.9–7.0(3H,m), 7.40(2h,dd,J=8,8Hz), 8.07(2H,dd,J=10,8Hz).

Example 13

2-(3,4-Dimethoxyphenyl)-2-(3-[4-(4-fluorobenzoyl)-1-piperidinyl]-1-propyl)-1,3-dithiane-1,1,3,3-tetraoxide
TLC(CHCl$_3$:MeOH=5:1).
R$_f$=0.58.
MS(FD,m/z) 567(M+).
H-NMR(TMS/CDCl$_3$, δ/ppm) 2.0–2.1(4H,m), 2.5–4.0(17H,m), 3.90(6H,s), 4.45(3H,t,J=10Hz), 6.91(1H,d,J=8Hz), 7.18(2H,dd,J=8,8Hz), 7.46(1H,dd,J=8,2Hz), 7.67(1H,d,J=2Hz), 7.93(2H,dd,J=10,8Hz).

Example 14

5-[4-(4-Dimethoxybenzoyl)-1-piperidinyl]-2-(3,4-dimethoxyphenyl)-2-isopropylvaleronitrile hydrochloride
TLC(CHCl$_3$:MeOH=9:1).
Rf=0.83.
MS(FD, m/z) 508(M+). H-NMR(TMS/CDCl$_3$, δ/ppm) 0.80(3H,t,J=6Hz), 1.21(3H,t,J=6Hz), 2.0–3.8(16H,m), 3.89(3H,s), 3.93(3H,s), 3.96(6H,s), 6.86(1H,d,J=8Hz), 6.91(1H,d,J=8Hz), 6.94(1H,d,J=2Hz), 7.00(1H,dd,J=8,2Hz), 7.44(1H,d,J=2Hz), 7.49(1H,dd,J=8,2Hz).

Example 15

2-(3,4-Dichlorophenyl)-5-[4-(4-fluorobenzoyl)-1-piperidinyl]-2-isopropylvaleronitrile hydrochloride
TLC(CHCl$_3$:MeOH=9:1).
Rf=0.88.
MS(FD,m/z) 474(M+).
H-NMR(TMS,CDCl$_3$, δ/ppm) 0.80(3H,d,J=8Hz), 1.22(3H,d,J=8Hz), 1.8–3.8(16H,m), 7.18(2H,dd,J=8,8Hz), 7.32(1H,dd,J=2,8Hz), 7.52(1H,d,J=8Hz), 7.58(1H,d,J=2Hz), 7.92(2H,dd,J=10,8Hz).

Example 16

5-[4-(5H-Dibenzo[a,d]cyclohepten-5-ylidene)-1-piperidinyl]-2-isopropylvaleronitrile hydrochloride
TLC(CHCl$_3$:MeOH=9:1).
Rf=0.90.
MS(FD, m/z) 532(M+).
H-NMR(TMS/CDCl$_3$, δ/ppm) 0.77(3H,d,J=8Hz), 1.18(3H,d,J=8Hz), 1.6–3.3(15H,m), 3.86(3H,s), 3.92(3H,s), 6.8–7.4(11H,m).

Example 17

2-(3-Benzoylphenyl)-5-[4-(4-fluorobenzoyl)-1-piperidinyl]-2-methyl-valeronitrile L-(+)-tartarate
TLC(CHCl$_3$:MeOH=9:1).
Rf=0.56.
MS(FD, m/z) 482(M+).
H-NMR(TMS/CDCl$_3$, δ/ppm) 1.4–1.6(1H,m), 1.6–1.9(5H,m), 1.77(3H,s), 2.0–2.2(4H,m), 2.37(2H, pseud t,J=7Hz), 2.8–3.0(2H,m), 3.3–3.6(2H,m), 4.45(1H,bs), 6.9–7.4(9H,m).

Example 18

2-(3,4-Dimethoxyphenyl)-5-[4-(α-hydroxy-4-fluorobenzyl)-1-piperidinyl]-2-isopropylvaleronitrile L-(+)-tartarate
TLC(CHCl$_3$:MeOH=9:1.
Rf=0.27.
MS(FD, m/z) 469(MH+).
H-NMR(TMS/CDCl$_3$, δ/ppm) 0.78(3H,d,J=7Hz), 1.1–1.2(4H,m), 1.16(3H,d,J=7Hz), 1.2–1.4(1H,m), 1.4–1.6(2H,m), 1.6–1.9(4H,m), 2.0–2.1(2H,m), 2.19(2H,pseud t,J=8Hz), 2.6–2.9(2H,m), 3.86(3H,s), 3.87(3H,s), 4.26(1H,d,J=7Hz), 6.8–7.1(5H,m), 7.1–7.3(2H,m).

Example 19

1-(4-Phenylbutyl)-α-(4-fluorophenyl)-4-piperidinemethanol L-(+)-tartarate
TLC(CHCl$_3$:MeOH=9:1)
Rf=0.21.
MS(FD,m/z) 341(M+).
H-NMR(TMS/CDCl$_3$, δ/ppm) 1.3–2.2(10H,m), 2.4–2.7(4H,m), 2.8–3.0(2H,m), 3.3–3.6(2H,m), 4.45(1H,bs), 6.9–7.4(9H,m).

Example 20

2,2-Diphenyl-5-[4-(4-fluorobenzoyl)-1-piperidinyl]-valeronitrile hydrochloride
TLC(CHCl$_3$:MeOH=9:1).
Rf=0.60.
MS(FD m/z) 440((M+).
H-NMR(TMS/CDCl$_3$, δ/ppm) 1.9–2.1(4H,m), 3.0–3.1(4H m), 3.2–3.3(2H,m), 3.7–3.8(1H,m), 7.18(2H,dd,J=8,8Hz), 7.2–7.5(10H,m), 7.92(2H,dd,J=10,8Hz).

Example 21

5-(4-[Bis(4-fluorophenyl)methylene]-1-piperidinyl)-2-(3,4-dimethoxyphenyl)-2-isopropylvaleronitrile hydrochloride
TLC(CHCl$_3$:MeOH=9:1).
Rf=0.54.
MS(FD,M/z) 544(M+).
H-NMR(TMS/CDCl$_3$, δ/ppm) 0.78(3H,d,J=8Hz), 1.20(3H,d,J=8Hz), 1.6-3.6(15H,m), 3.87(3H,s), 3.94(3H,s), 6.8-7.1(11H,m).

Example 22

2-(3,4-Dimethoxyphenyl)-6-4-(4-fluorobenzoyl)-1-piperidinyl]-2-isopropylhexanenitrile hydrochloride
TLC(CHCl$_3$:MeOH=9:1).
Rf=0.54.
MS (FD, m/z) 480((M+).
H-NMR(TMS/CDCl$_3$, δ/ppm) 0.80(3H,d,J=7Hz), 0.9-1.1(1H,m), 1.18(3H,d,J=7Hz), 1.3-1.7(3H,m), 1.8-1.9(5H,m), 2.0-2.2(4H,m), 2.30(2H,pseud t), 2.9-3.0(2H,m), 3.20(1H,pseud hept), 3.89(3H,s), 3.90(3H,s), 6.8-6.9(3H,m), 7.0-7.2(2H,m), 7.9-8.0(2H,m).

Example 23

2-(3,4-Dimethoxyphenyl)-2-isopropyl-5-[4(2,4,6-trimethylbenzoyl)-1-piperidinyl]valeronitrile hydrochloride
TLC(CHCl$_3$:MeOH=9:1).
RF=0.64.
MS (FD,m/z) 490(M+).
H-NMR(TMS/CDCl$_3$, δ/ppm) 0.8-1.3(6H,m), 1.9-3.6(25H,m), 3.9-4.0(6H,m), 6.8-7.0(5H,m).

Example 24

2-Dodecyl-5-[4-(4-fluorobenzoyl)-1-piperidinyl]-2-(3-methoxyphenyl)valeronitrile hydrochloride
TLC(CHCl$_3$:MeOH=9:1).
Rf=0.65.
MS (FD, m/z) 562(M+).
H-NMR(TMS/CDCl$_3$, δ/ppm) 0.88(3H,t,J=8Hz), 1.2-3.8(37H,m), 3.88(3H,s), 6.8-7.0(3H,m), 7.27(2H,dd,J=8,8Hz), 7.32(1H,dd,J=8,8Hz), 7.92(2H,dd,J=10,8Hz).

Example 25

5-[4-(4-Fluorobenzoyl)-1-piperidinyl]-2-phenylvaleronitrile hydrochloride
TLC(CHCl$_3$:MeOH=9:1).
Rf=0.54.
MS (FD, m/z) 364(M+).
H-NMR(TMS/CDCl$_3$, δ/ppm) 1.6-1.8(2H,m), 1.8-1.9(4H,m), 1.9-2.0(2H,m), 2.0-2.2(2H,m), 2.41(2H,t,J=7Hz), 2.9-3.0(2H,m), 3.20(1H,m), 3.88(1H,t,J=7Hz), 7.1-7.2(2H,m), 7.3-7.4(5H,m), 7.9-8.0(2H,m).

Example 26

2-(3-Chloropropyl)-5-[4-(4-Fluorobenzoyl)-1-piperidinyl]-2-phenylvaleronitrile hydrochloride
TLC(CHCl$_3$:MeOH=9:1).
Rf=0.61.
MS (FD,m/z) 440(M+).
H-NMR(TMS/CDCl$_3$, δ/ppm) 1.2-1.4(1H,m), 1.5-1.9 (4H,m), 1.9-2.2(7H,m), 2.31(2H,t,J=8Hz), 2.8-3.0(2H,m), 3.18(1H,m), 3.46(2H,t,J=6Hz), 7.0-7.2(2H,m), 7.3-7.5(5H,m), 7.9-8.0(2H,m).

Example 27

2-(3,4-Dimethoxyphenyl)-7-[4-(4-fluorobenzoyl)-1-piperidinyl]-2-isopropylheptanenitrile hydrochloride
TLC(CHCl$_3$:MeOH=9:1).
Rf=0.54.
MS (FD,m/z) 494(M+).
H-NMR(TMS/CDCl$_3$, δ/ppm) 0.80(3H,d,J=7Hz), 1.03(1H,m), 1.19(3H,d,J=7Hz), 1.2-1.5(5H,m), 1.7-1.9(5H,m), 2.0-2.2(4H,m), 2.28(2H,t), 2.9-3.0(2H,m), 3.20(1H,pseud quin), 3.88(3H,s), 3.90(3H,s), 6.8-7.0(3H,m), 7.1-7.2(2H,m), 7.9-8.0(2H,m).

Example 28

2-(3,4-Dimethoxyphenyl)-5-[4-(4-fluorobenzoyl)-1-piperidinyl]-2-phenylthiovaleronitrile hydrochloride
TLC(CHCl$_3$:MeOH=9:1).
Rf=0.69.
MS (FD, m/z) 532(M+).
H-NMR(TMS/CDCl$_3$, δ/ppm) 2.0-3.8(15H,m), 3.88(3H,S), 3.90(3H,s), 6.8-7.0(3H,m), 7.18(2H,dd,J=8,8Hz), 7.3-7.5(5H,m), 7.92(2H,dd,J=10,8Hz).

Example 29

5-[4-(4-Fluorobenzoyl)-1-piperidinyl]-2-isopropyl-2-(-1-naphthyl)valeronitrile hydrochloride
TLC(CHCl$_3$:MeOH=9:1).
Rf=0.68.
MS (FD,m/z) 456(M+).
H-NMR(TMS/CDCl$_3$, δ/ppm) 0.82(3H,bs), 1.35(3H,bs), 1.8-3.7(16H,m), 7.16(2H,dd,J=8,8Hz), 7.2-7.9(9H,m).

Example 30

5-[4-(4-Fluorobenzoyl)-1-piperidinyl]-2-isopropyl-2-(2-naphthyl)valeronitrile hydrochloride
TLC(CHCl$_3$:MeOH=9:1).
Rf=0.65.
MS (FD,m/z) 456(M+).
H-NMR(TMS/CDCl$_3$, δ/ppm) 0.80(3H,d,J=6Hz), 1.28(3H,d,J=6Hz), 1.5-3.7(16H,m), 7.1-8.0(11H,m).

Example 31

2-(3,4-Dimethoxyphenyl)-5-[4-(4-fluorophenyl)methylene-1-piperidinyl]-2-isopropylvaleronitrile hydrochloride
TLC(CHCl$_3$:MeOH=9:1).
Rf=0.73.
MS (FD,m/z) 450(M+).
H-NMR(TMS/CDCl$_3$, δ/ppm) 0.80(3H,d,J=8Hz), 1.20(3H,d,J=8Hz), 1.5-3.6(15H,m), 3.9-4.0(6H,m), 6.4-6.5(1H,m), 6.8-7.2(7H,m).

Example 32

5-[4-(4-Fluorobenzoyl)-1-piperidinyl]-2-isopropyl-2-(3-trifluoromethylphenyl)valeronitrile hydrochloride
TLC(CHCl$_3$:MeOH=9:1).
Rf=0.64.
MS (FD,m/z) 474(M+).
H-NMR(TMS/CDCl$_3$, δ/ppm) 0.80(3H,d,J=8Hz), 1.23(3H,d,J=8Hz), 1.7-1.8(1H,m), 2.0-3.4(14H,m), 3.7-3.8(1H,m), 7.18(2H,dd,J=8,8Hz), 7.6-7.7(3H,m), 7.92(2H,dd,J=10,8Hz).

Example 33

2-(3,4-Dimethoxyphenyl)-8-[4-(4-fluorobenzoyl)-1-piperidinyl]-2-isopropyloctanenitrile hydrochloride
TLC(CHCl$_3$:MeOH=9:1).
Rf=0.53.
MS (FD,m/z) 508(M+).
H-NMR(TMS/CDCl$_3$, δ/ppm) 0.80(3H,d,J-7Hz), 0.9-1.1(1H,m), 1.19(3H,d,7Hz), 1.2-1.5(10H,m), 1.7-1.9(5H,m), 2.0-2.2(4H,m), 2.33(2H,pseud t), 2.9-3.0(2H,m), 3.2(1H,pseud quin), 3.89(3H,s), 3.90(3H,s), 6.8-7.0(3H,m), 7.1-7.2(2H,m), 7.9-8.0(2H,m).

Example 34

5,6-Dimethoxy-1-(3-[4-(4-fluorobenzoyl)-1-piperidinyl]propyl)-1-indanenitrile hydrochloride
TLC(CHCl$_3$:MeOH=9:1).
Rf=0.74.
MS (FD,m/z) 450(M+).
H-NMR(TMS/CDCl$_3$, δ/ppm) 1.8-3.5(18H,m), 3.7-3.8(1H,m), 3.88(3H,s), 3.92(3H,s), 6.78(1H,s), 6.85(1H,s), 7.19(2H,dd,J=8,8Hz), 7.94(2H,dd,J=10,8Hz).

Example 35

2-(3,4-Dihydroxyphenyl)-2-dodecyl-5-[4-(4-fluorobenzoyl)-1-piperidinyl]-valeronitrile hydrochloride
TLC(CHCl$_3$:MeOH=9:1).
Rf=0.57.
MS (FD,m/z) 565(M+).
H-NMR(TMS/CDCl$_3$, δ/ppm) 0.88(3H,d,J=6Hz), 1.1-3.8(39H,m), 6.8-7.2(5H,m), 7.9-8.0(2H,m).

Example 36

2-(3,4-Dimethoxyphenyl)-2-dodecyl-5-[4-(α-hydroxy-4-fluorobenzyl)-1-piperidinyl]valeronitrile hydrochloride
TLC(CHCl$_3$:MeOH=9:1).
Rf=0.39.
MS (FD,m/z) 565(M+).
H-NMR(TMS/CDCl$_3$, δ/ppm) 0.88(3H,d,J=6Hz), 1.1-1.3(22H,m), 1.8-3.6(16H,m), 3.8-3.9(6H,m), 4.41(1H,d,J=8Hz), 6.8-7.3(7H,m).

Example 37

5-[4-(4-Fluorobenzoyl)-1-piperidinyl]-2-(1-methylpyrrole-2-yl)valeronitrile hydrochloride
TLC(CHCl$_3$:MeOH=9:1).
Rf=0.42.
MS (FD,m/z) 367(M+).
H-NMR(TMS/CDCl$_3$, δ/ppm) 1.7-1.9(6H,m), 1.9-2.2(4H,m), 2 4-2.5(2H,m), 2.9-3.1(2H,m), 3.21(1H,hep), 3.65(3H,s), 3.97(1H,dd,J=7,9Hz), 6.06-6.09(1H,m), 6.10-6.13(1H,m), 6.59-6.61(1H m), 7.10-7.17(2H,m), 7.93-7.99(2H,m).

Example 38

2-Butyl-2-(3,4-dimethoxyphenyl)-5-[4-(4-fluorobenzoyl)-1-piperidinyl]valeronitrile hydrochloride
TLC(CHCl$_3$:MeOH=9:1).
Rf=0.67.
MS (FD,m/z) 480(M+).
H-NMR(TMS/CDCl$_3$, δ/ppm) 0.86(3H,d,J=8Hz), 1.0-3.8(21H,m), 3.88(3H,s), 3.96(3H,s), 6.87(1H,d,J=8Hz), 6.92(1H,s), 6.99(1H,d,J=8Hz), 7.18(2H,dd,J=8,8Hz), 7.92(2H,dd,J=10,8Hz).

Example 39

2-(3,4-Dimethoxyphenyl)-5-[4-(4-fluorobenzoyl)-1-piperidinyl]-2-octylvaleronitrile hydrochloride
TLC(CHCl$_3$:MeOH=9:1).
Rf=0.70.
MS (FD,m/z) 536(M+).
H-NMR(TMS/CDCl$_3$, δ/ppm) 0.86(3H,d,J=8Hz), 1.0-3.8(14H,m), 3.88(3H,s), 3.96(3H,s), 6.87(1H,d,J=8Hz), 6.92(1H,d,J=2Hz), 6.99(1H,dd,J=8,2Hz), 7.18(2H,dd,J=8,8Hz), 7.90(2H,dd,J=10,8Hz).

Example 40

5-[4-(4-Fluorobenzoyl)-1-piperidinyl-2-isopropyl-2-(1-methylpyrrole-2-yl)valeronitrile hydrochloride
TLC(CHCl$_3$:MeOH=9:1).
Rf=0.54.
MS (FD,m/z) 409(M+).
H-NMR(TMS/CDCl$_3$, δ/ppm) 1.00(3H,d,J=7Hz), 1.08(3H,d,J=7Hz), 1.4-1.5(1H,m), 1.5-1.7(1H,m), 1.7-1.9(4H,m), 1.9-2.1(4H,m), 2.24(1H,hept,J=7Hz), 2.3-2.4(2H,m), 2.8-2.9(2H,m), 3.18(1H,hep), 3.74(3H,s), 6.00-6.03(1H,m), 6.10-6.14(1H,m), 6.52-6.54(1H,m), 7.09-7.16(2H,m), 7.93-7.98(2H,m).

Example 41

2-(3,4-Dimethoxyphenyl)-5-[4-(4-fluorobenzoyl)-1-piperidinyl]-2-hexadecylvaleronitrile hydrochloride
TLC(CHCl$_3$:MeOH=9:1).
Rf=0.76.
MS (FD,m/z) 648(M+).
H-NMR(TMS/CDCl$_3$, δ/ppm) 0.88(3H,t,J=8Hz), 1.0-3.8(45H,m), 3.88(3H,s), 3.96(3H,s), 6.86(1H,d,J=8Hz), 6.92(1H,s), 6.99(1H,d,J=8Hz), 7.18(2H,dd,J=8,8Hz), 7.91(2H,dd,J=10,8Hz).

Example 42

2-(3,4-Dimethoxyphenyl)-5-[4-(4-fluorobenzoyl)-1-piperidinyl]-2-methylvaleronitrile

Example 43

2-(3,4-Dimethoxyphenyl)-2-ethyl-5-[4-(4-fluorobenzoyl)-1-piperidinyl]valeronitrile

Example 44

2-(3,4-Dimethoxyphenyl)-5-[4-(4-fluorobenzoyl)-1-piperidinyl]-2-propylvaleronitrile

Example 45

2-(3 4-Dimethoxyphenyl)-5-[4-(4-fluorobenzoyl)-1-piperidinyl]-2-pentylvaleronitrile

Example 46

2-(3,4-Dimethoxyphenyl)-5-[4-(4-fluorobenzoyl)-1-piperidinyl]-2-hexylvaleronitrile

Example 47

2-(3,4-Dimethoxyphenyl)-5-[4-(4-fluorobenzoyl)-1-piperidinyl]-2-heptylvaleronitrile

Example 48

2-(3,4-Dimethoxyphenyl)-5-[4-(4-fluorobenzoyl)-1-piperidinyl]-2-nonylvaleronitrile

Example 49

2-Decyl-2-(3,4-Dimethoxyphenyl)-5-[4-(4-fluorobenzoyl)valeronitrile

Example 50
2-(3,4-Dimethoxyphenyl)-5-[4-(4-fluorobenzoyl)-1-piperidinyl]-2-undecylvaleronitrile

Example 51
2-(3,4-Dimethoxyphenyl)-5-[4-(4-fluorobenzoyl)-1-piperidinyl]-2-tridecylvaleronitrile

Example 52
2-(3,4-Dimethoxyphenyl)-5-[4-(4-fluorobenzoyl)-1-piperidinyl]-2-tetradecylvaleronitrile

Example 53
2-(3,4-Dimethoxyphenyl)-5-[4-(4-fluorobenzoyl)-1-piperidinyl]-2-pentadecylvaleronitrile

Example 54
2-Allyl-2-(3,4-Dimethoxyphenyl)-5-[4-(4-fluorobenzoyl)-1-piperidinyl]valeronitrile

Example 55
2-Cyclopropyl-2-(3,4-Dimethoxyphenyl)-5-[4-(4-fluorobenzoyl)-1-piperidinyl]valeronitrile

Example 56
2-Cyclobutyl-2-(3,4-Dimethoxyphenyl)-5-[4-(4-fluorobenzoyl)-1-piperidinyl]valeronitrile

Example 57
2-Cyclopentyl-2-(3,4-Dimethoxyphenyl)-5-[4-(4-fluorobenzoyl)-1-piperidinyl]valeronitrile

Example 58
2-Cyclohexyl-2-(3,4-Dimethoxyphenyl)-5-[4-(4-fluorobenzoyl)-1-piperidinyl]valeronitrile

Example 59
2-Cyclooctyl-2-(3,4-Dimethoxyphenyl)-5-[4-(4-fluorobenzoyl)-1-piperidinyl]valeronitrile

Example 60
2-(3,4-Dimethoxyphenyl)-3-[4-(4-fluorobenzoyl)-1-piperidinyl]-2-(3-pentyl)valeronitrile

Example 61
2-(3,4-Dimethoxyphenyl)-3-[4-(4-fluorobenzoyl)-1-piperidinyl]-2-(4-heptyl)valeronitrile

Example 62
2-(3,4-Dimethoxyphenyl)-5-[4-(4-fluorobenzoyl)-1-piperidinyl]-2-phenylvaleronitrile

Example 63
2-Benzyl-2-(3,4-dimethoxyphenyl)-5-[4-(4-fluorobenzoyl)-1-piperidinyl]valeronitrile

Example 64
2-(3,4-Dimethoxyphenyl)-3-[4-(4-fluorobenzoyl)-1-piperidinyl]-2-(1-naphthyl)valeronitrile

Example 65
2-(3,4-Dimethoxyphenyl)-3-[4-(4-fluorobenzoyl)-1-piperidinyl]-2-(2-naphthyl)valeronitrile

Example 66
2-(3,4-Dimethoxyphenyl)-3-[4-(4-fluorobenzoyl)-1-piperidinyl]-2-dodecylpropionitrile

Example 67
2-(3,4-Dimethoxyphenyl)-4-[4-(4-fluorobenzoyl)-1-piperidinyl]-2-dodecylbutyronitrile

Example 68
2-(3,4-Dimethoxyphenyl)-6-[4-(4-fluorobenzoyl)-1-piperidinyl]-2-dodecylhexanenitrile

Example 69
2-(3,4-Dimethoxyphenyl)-7-[4-(4-fluorobenzoyl)-1-piperidinyl]-2-dodecylheptanenitrile

Example 70
2-(3,4-Dimethoxyphenyl)-8-[4-(4-fluorobenzoyl)-1-piperidinyl]-2-dodecyloctanenitrile

Example 71
5-(4-[Bis(4-fluorophenyl)methylene]-1-piperidinyl)-2-(3,4-dimethoxyphenyl)-2-dodecylvaleronitrile

Example 72
2-(3,4-Dimethoxyphenyl)-5-[4-(4-fluorobenzyl)-1-piperidinyl]-2-dodecylvaleronitrile

Example 73
5-(4-Benzyl-1-piperidinyl)-2-(3,4-dimethoxyphenyl)-2-dodecylvaleronitrile

Example 74
5-(4-Benzoyl-1-piperidinyl)-2-(3,4-dimethoxyphenyl)-2-dodecylvaleronitrile

Example 75
2-(3,4-Dimethoxyphenyl)-5-[4-(4-fluorobenzoyl)-1-piperadinyl]-2-dodecylvaleronitrile

Example 76
5-[4-(5H-Dibenzo(a,d)cyclohepten-5-ylidene)-1-piperidinyl]-2-dodecylvaleronitrile

Example 77
5-[4-(4-Dimethoxybenzoyl)-1-piperidinyl]-2-(3,4-dimethoxyphenyl)-2-dodecylvaleronitrile

Example 78
5-[4-(3,4-Dichlorophenyl)-2-dodecyl-5-[4-(4-fluorobenzoyl)-1-piperidinyl]valeronitrile

Example 79
2-(3,4-Dimethoxyphenyl)-2-dodecyl-5-[4-(2,4,6-trimethylbenzoyl)-1-piperidinyl]valeronitrile

Example 80
5-[4-(4-Fluorobenzoyl)-1-piperidinyl]-2-dodecyl-2-(1-naphthyl)valeronitrile

Example 81
5-[4-(4-Fluorobenzoyl)-1-piperidinyl]-2-dodecyl-2-(2-naphthyl)valeronitrile

Example 82
2-(3,4-Dimethoxyphenyl)-2-dodecyl-5-[4-(4-fluorophenyl)methylene-1-piperidinyl]valeronitrile

Example 83
5-[4-(4-Fluorobenzoyl)-1-piperidinyl]-2-dodecyl-2-(3-trifluoromethylphenyl)valeronitrile

Example 84

5-[4-(4-Fluorobenzoyl)-1-piperidinyl]-2-dodecyl-2-(1-methylpyrrole-2-yl)valeronitrile

Example 85

2-(3,4-Dimethoxyphenyl)-5-[4-(α-hydroxy-4-fluorobenzyl)-1-piperidinyl]-2-methylvaleronitrile

Example 86

2-(3,4-Dimethoxyphenyl)-2-ethyl-5-[4-(α-hydroxy-4-fluorobenzyl)-1-piperidinyl]valeronitrile

Example 87

2 (3,4-Dimethoxyphenyl)-5-[4-(α-hydroxy-4-fluorobenzyl)-1-piperidinyl]-2-propylvalerontrile

Example 88

2-Butyl-2-(3,4-Dimethoxyphenyl)-5-[4-(α-hydroxy-4-fluorobenzyl)-1-piperidinyl]valeronitrile

Example 89

2-(3,4-Dimethoxyphenyl)-5-[4-(α-hydroxy-4-fluorobenzyl)-1-piperidinyl]-2-pentylvaleronitrile

Example 90

2-(3,4-Dimethoxyphenyl)-2-hexyl-5-[4-(α-hydroxy-4-fluorobenzyl)-1-piperidinyl]valeronitrile

Example 91

2-(3,4-Dimethoxyphenyl)-2-heptyl-5-[4-(α-hydroxy 4-fluorobenzyl)-1-piperidinyl]valeronitrile

Example 92

2-(3 4-Dimethoxyphenyl)-5-[4-(α-hydroxy-4-fluorobenzyl)-1-piperidinyl]-2-octylvaleronitrile

Example 93

2-(3,4-Dimethoxyphenyl)-5-[4-(α-hydroxy-4-fluorobenzyl)-1-piperidinyl]-2-nonylvaleronitrile

Example 94

2-Decyl-2-(3,4-Dimethoxyphenyl)-5-[4-(α-hydroxy-4-fluorobenzyl)-1-piperidinyl]valeronitrile

Example 95

2-(3,4-Dimethoxyphenyl)-5-[4-(α-hydroxy-4-fluorobenzyl)-1-piperidinyl-2-undecylvaleronitrile

Example 96

2-( 3,4-Dimethoxyphenyl)-5-[4-(α-hydroxy-4-fluorobenzyl)-1-piperidinyl]tetradecylvaleronitrile

Example 97

2-(3,4-Dimethoxyphenyl)-2-dodecyl-4-[4-(α-hydroxy-4-fluorobenzyl)-1-piperidinyl]butyronitrile

Example 98

2-(3,4-Dimethoxyphenyl)-2-dodecyl-6-[4-(α-hydroxy-4-fluorobenzyl)-1-piperidinyl]hexanenitrile

Example 99

2-(3,4-Dimethoxyphenyl)-2-dodecyl-7-[4-(α-hydroxy-4-fluorobenzyl)-1-piperidinyl]-heptanenitrile

Example 100

2-(3,4-Dimethoxyphenyl)-2-dodecyl-8-[4-(α-hydroxy-4-fluorobenzyl)-1-piperidinyl]-octanenitrile

Example 101

5-(3-[4-(4-Fluorobenzoyl)-1-piperidinyl]propyl)-2,3-dihydro-3-hydroxy-2-phenyl-1,5-benzothiazepine-4(5H)-on

Example 102

5-(3-[4-(4-Fluorobenzoyl)-1-piperidinyl]propyl)-2,3-dihydro-3-hydroxy-2-phenyl-1,5-benzothiazepine-4(5H)-on acetate L-(+)-tartarate

Example 103

4-[4-(4-Fluorobenzoyl)-1-piperidinyl]-(3,4-dimethoxyphenyl)butyrophenone

Example 104

4-[4-(5H,Dibenzo[a,d]cyclohepten-5-ylidene)-1-piperidinyl]-4'-fluorobutyrophenone

Example 105

2-(3,4-Dimethoxyphenyl)-2-isopropyl-5-(4-phenyl-1-piperidinyl)valeronitrile

Example 106

2,2-Bis{3-[4-fluorobenzoyl)-1-piperidinyl]-1-propyl}-(3-methoxyphenyl)acetonitrile

Example 107

2-(3-[N-((3,4-Dimethoxyphenyl)-N-methylamino]-1-propyl)-2-(3,4-dimethoxyphenyl)-5-[4-(4-fluorobenzoyl)-1-piperidinyl]valeronitrile

Example 108

3-(2-[4-(4-Fluorobenzoyl)-1-piperidinyl]-1-ethyl]-5-(2-methoxy-1-ethyl)-2,6-dimethyl-4-(3-nitrophenyl)-1,4-dihydropyridine-3,5-dicarboxylate.

Example 109

Evaluation of Serotonin-Antagonistic Activity

SD male rats (from 8th to 12th week-age, weight: about 300 g) were killed and the abdomen of each rat was cut to remove the aorta. The aorta was cut into 2.5 pieces and hung in a M gnus' tube kept at 37°±1° C. and containing 20 ml of a K.S. Linger solution, into which a mixed gas of 95% $O_2$+5% $CO_2$ was introduced. These specimens were connected to an isotonic transducer and recorded under a load of 1 g. The concentration of serotonin was from $1 \times 10^{-7}$M to $1 \times 10^{-4}$M; and the concentration of the product to be tested was from $1 \times 10^{-4}$M to $1 \times 10^{-3}$M. From the serotinin dose-reaction curve, $pA_2$ was calculated by Van Rossem et al's method. The affinity for the 5-$HT_2$ receptor was evaluated by receptor binding assay used by the microsomal fraction of the bovine cortex. The results are summarized in Table 1.

TABLE 1

| Example No. | Serotonin-antagonistic Activity (*$pA_2$, pki) |
|---|---|
| 3 | 8.3* |
| 4 | 8.2* |
| 5 | 8.2* |
| 6 | 8.5* |
| 7 | 8.5* |
| 8 | 8.0* |
| 9 | 8.0* |
| 10 | 7.3* |
| 11 | 7.7* |
| 20 | 7.6* |

TABLE 1-continued

| Example No. | Serotonin-antagonistic Activity (*pA$_2$, pki) |
|---|---|
| 25 | 8.9 |
| 26 | 8.9 |
| 38 | 7.8 |

Example 110

Evaluation of Blood Antihypertive Activity

Six male SHR rats which had been bred under sufficient acclimation and were ascertained to be hypertensive (spontaneous hypertensive rats, weight: 400–440 g) were used as test animals.

A 1 ml amount of a physiological salt solution containing the product to be tested (10 mg/kg) in 2.5% of Nicol and 2.5% of ethanol was intravenously injected into each rat once. The blood pressure of the test animal was measured by a closed (bloodless) blood pressure measuring method. The results are summarized in Table 2.

TABLE 2

| Exp No. | Dose (mg/kg) | Reduction of Blood Pressure (mmHg) Time After Administration | |
|---|---|---|---|
| | | 0.5 hr | 4 hr |
| 1 | 10 | −19 | −8 |
| 2 | 10 | −41 | −10 |
| 3 | 10 | −7 | −8 |
| 4 | 10 | −4 | −12 |
| 5 | 10 | −91 | −37 |
| 6 | 10 | −84 | −34 |
| 7 | 10 | −30 | 6 |
| 8 | 10 | −84 | 9 |
| 9 | 10 | −89 | −30 |
| 10 | 10 | −89 | −30 |
| 11 | 10 | −91 | −26 |
| 12 | 10 | −94 | −47 |
| 13 | 10 | −43 | −6 |
| 14 | 10 | −15 | −9 |
| 15 | 10 | −102 | −25 |
| 16 | 10 | −61 | −11 |
| 17 | 10 | −65 | −3 |
| 18 | 10 | −17 | −13 |
| 19 | 10 | −47 | −17 |
| 21 | 10 | −43 | −21 |
| 23 | 10 | −27 | −13 |
| 25 | 3 | −108 | −35 |
| 26 | 10 | −85 | −21 |
| 27 | 10 | −61 | −2 |
| 28 | 10 | −63 | −3 |
| 29 | 10 | −110 | −53 |
| 30 | 10 | −45 | −9 |
| 31 | 10 | −85 | −11 |
| 32 | 10 | −49 | −10 |
| 33 | 10 | −36 | −12 |
| 34 | 10 | −102 | −22 |
| 35 | 10 | −69 | −20 |
| 36 | 10 | −118 | −95 |
| 37 | 10 | −95 | −25 |
| 38 | 10 | −82 | −38 |
| 39 | 10 | −117 | −50 |
| 40 | 10 | −80 | −25 |
| 41 | 10 | −35 | −10 |
| 43 | 10 | −68 | −27 |
| 46 | 10 | −144 | −77 |
| 49 | 10 | −157 | −91 |
| 52 | 10 | −22 | −12 |
| 68 | 10 | −145 | −99 |
| 69 | 10 | −108 | −78 |
| 70 | 10 | −41 | −45 |
| 71 | 10 | −9 | −22 |
| 73 | 10 | −90 | −57 |
| 74 | 3 | −34 | −13 |
| 75 | 10 | −7 | −9 |
| 76 | 10 | −40 | −70 |
| 77 | 3 | −49 | −17 |
| 79 | 10 | −14 | −14 |
| 82 | 10 | −35 | −22 |
| 86 | 10 | −25 | −8 |
| 88 | 10 | −82 | −38 |
| 90 | 10 | −120 | −58 |
| 92 | 10 | −136 | −101 |
| 94 | 10 | −109 | −67 |
| 96 | 10 | −62 | −62 |
| 98 | 30 | −144 | −140 |
| 99 | 10 | −62 | −74 |
| 100 | 10 | −41 | −45 |
| 102 | 10 | −18 | −3 |
| 103 | 10 | −47 | −17 |
| 104 | 10 | −93 | −14 |
| 105 | 10 | −44 | −64 |
| 106 | 10 | −36 | −8 |
| 107 | 10 | −51 | −6 |
| 108 | 10 | −156 | −100 |

Evaluation of the Data

From the above results, it is understood that the ethylamine derivative of the present invention has both serotonine-antagonistic activity and antihypertensive activity and can therefore be used as an antihypertensive agent. Accordingly, it is believed that the present compound in use will provide excellent antihypertensive effects.

Unless otherwise indicated, developing conditions for TLC were under chloroform/methanol=9/1; mass spectrum (MS) was performed in FD mode (m/z) and nuclear magnetic resonance spectrum (NMR) was measured using tetramethylsilane as the internal standard and deuterium chloroform as the solvent.

Example 111

2-Decyl-2-(3,4-dimethoxyphenyl)-5-(4-(α-hydroxy-4-fluoro-benzyl)-1-piperidinyl)valeronitrile hydrochloride TLC Rf=0.29.

MS 566 (M+).

NMR 0.88 (3H, t), 1.1–1.3 (18H, m), 1.8–3.6 (16H, m), 3.8–3.9 (6H, m), 4.41 (1H, d), 6.8–7.3 (7H, m).

Example 112

2-(3,4-Dimethoxyphenyl)-5-(4-(α-hydroxy-4-fluorobenzyl)-1-piperidinyl)-2-tridecylvaleronitrile hydrochloride TLC Rf=0.38.

MS 608 (M+).

NMR 0.88 (3H, t), 1.1–1.3 (24H, m), 1.8–3.6 (16H, m), 3.8–3.9 (6H, m), 4.41 (1H, d), 6.8–7.3 (7H, m).

Example 113

2-Decyl-2-(3,4-dimethoxyphenyl)-6-(4-(4-fluorobenzoyl)-1-piperidinyl)hexanenitrile hydrochloride TLC Rf=0.71.

MS 578 (M+).

NMR 0.84 (3H, t), 1.2–1 5 (18H, m), 1.6–2.1 (10H, m), 2.9–3.1 (4H, m), 3.4–3.5 (2H, m), 3.6–3.8 (1H,m), 3.77 (3H, s), 3.79 (3H, s), 6.9–7.0 (3H, m), 7.41 (2H, dd), 8.03 (2H, dd).

Example 114

2-(3,4-Dimethoxyphenyl)-6-(4-(4-fluorobenzoyl)-1-piperidinyl)-2-undecylhexanenitrile hydrochloride TLC Rf=0.71.
MS 592 (M+).
NMR 0.84 (3H, t), 1.2–1.5 (20H, m), 1.6–2.1 (10H, m), 2.9–3.1 (4H, m), 3.4–3.5 (2H, m), 3.6–3.8 (1H, m), 3.77 (3H, s), 3.79 (3H, s), 6.9–7.0 (3H, m), 7.43 (2H, dd), 7.99 (2H, dd).

Example 115

2-(3,4-Dimethoxyphenyl)-6-(4-(4-fluorobenzoyl)-1-piperidinyl)-2-tridecylhexanenitrile hydrochloride
TLC Rf=0.72.
MS 620 (M+).
NMR 0.84 (3H, t), 1.2–1.5 (24H, m), 1.6–2.1 (10H, m), 2.9–3.1 (4H, m), 3.4–3.5 (2H, m), 3.6–3.8 (1H, m), 3.76 (3H, s), 3.79 (3H, s), 6.9–7.0 (3H, m), 7.44 (2H, dd), 8.01 (2H, dd).

Example 116

2-(3,4-Dimethoxyphenyl)-6-(4-(4-fluorobenzoyl)-1-piperidinyl)-2-tetradecylhexanenitrile hydrochloride
TLC Rf=0.73.
MS 634 (M+).
NMR 0.84 (3H, t), 1.2–1.5 (24H, m), 1.6–2.1 (10H, m), 2.9–3.1 (4H, m), 3.4–3.5 (2H, m), 3.6–3.8 (1H, m), 3.76 (3H, s), 3.79 (3H, s), 6.9–7.0 (3H, m), 7.41 (2H, dd), 8.02 (2H, dd).

Example 117

2-Decyl-2-(3,4-dimethoxyphenyl)-6-(4-(α-hydroxy-4-fluorobenzyl)-1-piperidinyl)hexanenitrile hydrochloride
TLC Rf=0.39.
MS 580 (M+).
NMR 0.87 (3H, t), 1.1–1.3 (18H, m), 1.8–3.6 (18H, m), 3.8–3.6 (18H, m), 3.8–3.9 (6H, m), 4.41 (1H, d), 6.8–7.3 (7H, m).

Example 118

2-(3,4-Dimethoxyphenyl)-6-(4-(α-hydroxy-4-fluorobenzyl)-1-piperidinyl)-2-undecylhexanenitrile hydrochloride
TLC Rf=0.39.
MS 594 (M+).
NMR 0.87 (3H, t , 1.1–1.3 (20H, m), 1.8–3.6 (18H, m), 3.8–3.9 (6H, m), 4.41 (1H, d), 6.8–7.3 (7H, m).

Example 119

2-(3,4-Dimethoxyphenyl)-6-(4-(α-hydroxy-4-fluorobenzyl)-1-piperidinyl)-2-tridecylhexanenitrile hydrochloride
TLC Rf=0.40.
MS 622 (M+).
NMR (fee base) 0.87 (3H, t), 1.1–1.3 (24H, m), 1.8–3.6 (18H, m), 3.8–3.9 (6H, m), 4.44 (1H, d), 6.8–7.3 (7H, m).

Example 120

2-(3,4-Dimethoxyphenyl)-6-(4-(α-hydroxy-4-fluorobenzyl)-1-piperidinyl)-2-tetradecylhexanenitrile hydrochloride
TLC Rf=0.41.
MS 636 (M+).
NMR (free base) 0.87 (3H, t), 1.1–1.3 (26H, m), 1.8–3.6 (18H, m), 3.8–3.9 (6H, m), 4.43 (1H, d), 6.8–7.3 (7H, m).

Example 121

2-Decyl-2-(3,4-dimethoxyphenyl)-7-(4-(4-fluorobenzoyl)-1-piperidinyl)heptanenitrile hydrochloride
TLC Rf=0.69.
MS 592 (M+).
NMR (free base) 0.81 (3H, t), 1.2–1.5 (18H, m), 1.6–2.2 (12H, m), 2.9–3.1 (4H, m), 3.4–3.5 (2H, m), 3.6–3.8 (1H, m), 3.77 (3H, s), 3.78 (3H, s), 6.9–7.0 (3H, m), 7.42 (2H, dd), 8.02 (2H, dd).

Example 122

2-(3,4-Dimethoxyphenyl)-7-(4-(4-fluorobenzoyl)-1-piperidinyl)-2-undecylheptanenitrile hydrochloride
TLC Rf=0.69.
MS 606 (M+).
NMR (free base) 0.84 (3H, t), 1.2–1.5 (20H, m), 1.6–2.2 (12H m), 2.9–3.1 (4H, m), 3.4–3.5 (2H, m), 3.6–3.8 (1H, m), 3.77 (3H, s), 3.78 (3H, s) 6.9–7.0 (3H, m , 7.41 (2H, dd), 8.04 (2H, dd).

Example 123

2-(3,4-Dimethoxyphenyl)-7-(4-(4-fluorobenzoyl)-1-piperidinyl)-2-tridecylheptanenitrile hydrochloride
TLC Rf=0.74.
MS 634 (M+).
NMR (free base) 0.84 (3H, t), 1.2–1.5 (24H, m), 1.6–2.2 (12H, m), 2.9–3.2 (4H, m), 3.4–3.5 (2H, m), 3.6–3.8 (1H, m), 3.77 (3H, s), 3.80 (3H, s), 6 9–7.0 (3H, m), 7.44 (2H, dd), 8.10 (2H, dd).

Example 124

2-(3,4-Dimethoxyphenyl)-7-(4-(4-fluorobenzoyl)-1-piperidinyl)-2-tetradecylheptanenitrile hydrochloride
TLC Rf=0.72.
MS 648 (M+).
NMR 0.85 (3H, t), 1.2–1.5 (26H, m), 1.6–2.2 (12H, m), 2.9–3.1 (4H, m), 3.4–3.5 (2H, m), 3.6–3.8 (1H, m), 3.76 (3H, s), 3.81 (3H, s), 6.9–7.0 (3H, m), 7.44 (2H, dd), 8.10 (2H, dd).

Example 125

2-Decyl-2-(3,4-dimethoxyphenyl)-7-(4-(α-hydroxy-4-fluorobenzyl)-1-piperidinyl)heptanenitrile hydrochloride
TLC Rf=0.41.
MS 594 (M+).
NMR 0.87 (3H, t), 1.1–1.3 (18H, m), 1.8–3.6 (20H, m), 3.8–3.9 (6H, m), 4.39 (1H, d), 6.8–7.3 (7H, m).

Example 126

2-(3,4-Dimethoxyphenyl)-7-(4-(α-hydroxy-4-fluorobenzyl)-1-piperidinyl)-2-undecylheptanenitrile hydrochloride
TLC Rf=0.39.
MS 608 (M+).
NMR 0.89 (3H, t), 1.1–1.3 (20H, m), 1.8–3.6 (20H, m), 3.8–3.9 (6H, m), 4.44 (1H, d), 6.8–7.3 (7H, m).

Example 127

2-(3,4-Dimethoxyphenyl)-7-(4-(α-hydroxy-4-fluorobenzoyl)-1-piperidinyl)-2-tridecylheptanenitrile hydrochloride
TLC Rf=0.45.
MS 636 (M+).
NMR 0.85 (3H, t), 1.1–1.3 (24H, m), 1.8–3.6 (20H, m), 3.8–3.9 (6H, m), 4.40 (1H, d), 6.8–7.4 (7H, m).

Example 128

2-(3,4-Dimethoxyphenyl)-7-(4-(α-hydroxy-4-fluorobenzoyl)-1-piperidinyl)-2-tetradecylheptanenitrile hydrochloride TLC Rf=0.46.
MS 650 (M+).
NMR 0.85 (3H, t), 1.1–1.3 (26H, m), 1.8–3.6 (20H, m), 3.8–3.9 (6H, m), 4.41 (3H, d), 6.8–7.3 (7H, m).

Example 129

2-Decyl-2-(3,4-dimethoxyphenyl)-8-(4-(4-fluorobenzoyl)-1-piperidinyl)octanenitrile hydrochloride
TLC Rf=0.71.
MS 606 (M+).
NMR 0.88 (3H, t), 1.2–1.5 (18H, m), 1.6–2.2 (14H, m), 2.9–3.1 (4H, m), 3.4–3.5 (2H, m), 3.6–3.8 (1H, m), 3.78 (3H, s), 3.79 (3H, s), 6.9–7.0 (3H, m), 7.44 (2H, dd), 8.03 (2H, dd).

Example 130

2-(3,4-Dimethoxyphenyl)-7-(4-(4-fluorobenzoyl)-1-piperidinyl)-2-undecylic acid nitrile hydrochloride
TLC Rf=0.78.
MS 620 (M+).
NMR 0.87 (3H, t), 1.2 1.5 (20H, m), 1.6–2.2 (14H, m), 2.9–3.1 (4H, m), 3.4–3.5 (2H, m), 3.6–3.8 (1H, m), 3.78 (3H, s), 3.79 (3H, s), 6.9–7.0 (3H, m), 7.44 (2H, dd), 8.03 (2H, dd).

Example 131

2-(3,4-Dimethoxyphenyl)-8-(4-(4-fluorobenzoyl)-1-piperidinyl)-2-tridecyloctanenitrile hydrochloride
TLC Rf=0.70.
MS 648 (M+).
NMR 0.84 (3H, t), 1.1–1.5 (24H, m), 1.6–2.2 (14H, m), 2.9–3.1 (4H, m), 3.4–3.5 (2H, m), 3.6–3.8 (1H, m), 3.78 (3H, s), 3.79 (3H, s), 6.9–7.0 (3H, m), 7.41 (2H, dd), 8.03 (2H, dd).

Example 132

2-(3,4-Dimethoxyphenyl)-8-(4-(4-fluorobenzoyl)-1-piperidinyl)-2-tetradecyloctanenitrile hydrochloride
TLC Rf=0.70.
MS 662 (M+).
NMR 0.84 (3H, t), 1.1–1.5 (24H, m), 1.6–2.2 (14H, m), 2.9–3.1 (4H, m), 3.4–3.5 (2H, m), 3.6–3.8 (1H, m), 3.78 (3H, s), 3.79 (3H, s), 6.9–7.0 (3H, m), 7.41 (2H, dd), 8.03 (2H, dd).

Example 133

2-Decyl-2-(3,4-dimethoxyphenyl)-8-(4-(α-hydroxy-4-fluorobenzyl)-1-piperidinyl)octanenitrile hydrochloride
TLC Rf=0.41.
MS 608 (M+).
NMR 0.85 (3H, t), 1.1–1.3 (18H, m), 1.8–3.6 (22H, m), 3.8–3.9 (6H, m), 4.42 (1H, d), 6.8–7.3 (7H, m).

Example 134

2-(3,4-Dimethoxyphenyl)-8-(4-(α-hydroxy-4-fluorobenzyl)-1-piperidinyl)-2-undecyloctanenitrile hydrochloride
TLC Rf=0.45.
MS 622 (M+).
NMR 0.85 (3H, t), 1.1–1.3 (20H, m), 1.8–3.6 (22H, m), 3.8–3.9 (6H, m), 4.43 (1H, d), 6.8–7.3 (7H, m).

Example 135

2-(3,4-Dimethoxyphenyl)-8-(4-(α-hydroxy-4-fluorobenzyl)-1-piperidinyl)-2-tridecylnitrile hydrochloride
TLC Rf=0.44.
MS 650 (M+).
NMR 0.88 (3H, t), 1.1–1.3 (24H, m), 1.8–3.6 (22H, m), 3.8–3.9 (6H, m), 4.45 (1H, d), 6.8–7.3 (7H, m).

Example 136

2-(3,4-Dimethoxyphenyl)-8-(4-(α-hydroxy-4-fluorobenzyl)-1-piperidinyl)-2-tetradecylnitrile hydrochloride
TLC Rf=0.42.
MS 664 (M+).
NMR 0.88 (3H, t), 1.1–1.3 (26H, m), 1.8–3.6 (22H, m), 3.8–3.9 (6H,m), 4.41 (1H, d), 6.8–7.3 (7H, m).

Example 137

2-(3,4-Dimethoxyphenyl)-2-dodecyl-4-(4-(4-fluorobenzoyl)-1-piperidinyl)butanenitrile hydrochloride
TLC Rf=0.71.
MS 578 (M+).
NMR 0.85 (3H, t), 1.2–1.5 (22H, m), 1.6–2.2 (6H, m), 2.9–3.1 (4H, m), 3.4–3.5 (2H, m), 3.6–3.8 (1H, m), 3.78 (3H, s), 3.79 (3H, s), 6 9–7.0 (3H, m), 7.41 (2H, dd), 8.03 (2H, dd).

Example 138

2-(3,4-Dimethoxyphenyl)-2-dodecyl-4-(4-(4-fluorobenzoyl)-1-piperidinyl)butanenitrile hydrochloride
TLC Rf=0.37.
MS 580 (M+).
NMR 0.87 (3H, t), 1.1–1.3 (22H, m), 1.8–3.6 (12H, m), 3.8–3.9 (6H, m), 4.44 (1H, d), 6.8–7.3 (7H, m).

Example 139

2-Dodecyl-2-(4-methoxyphenyl)-5-(4-(4-fluorobenzoyl)-1-piperidinyl)valeronitrile hydrochloride
TLC Rf=0.78.
MS 562 (M+).
NMR 0.83 (3H, t), 1.2–1.5 (22H, m), 1.6–2.2 (8H, m), 2.9–3.1 (4H, m), 3.4–3.5 (2H, m), 3.6–3.8 (1H, m), 3.79 (3H, s), 7.0–8.0 (8H, m).

Example 140

2-Dodecyl-5-(4-(4-fluorobenzoyl)-1-piperidinyl)-2-phenyl-valeronitrile hydrochloride
TLC Rf=0.79.
MS 532 (M+).
NMR 0.83 (3H, t), 1.2–1.5 (22H, m), 1.6–2.2 (8H, m), 2.9–3.1 (4H, m), 3.4–3.5 (2H, m), 3.6–3.8 (1H, m), 7.0–8.0 (9H, m).

Example 141

2-(3,4-Dimethoxyphenyl)-2-dodecyl-5-(4-(α-hydroxybenzyl)-1-piperidinyl)valeronitrile hydrochloride
TLC Rf=0.40.
MS 576 (M+).
NMR 0.88 (3H, t), 1.1–1.3 (22H, m), 1.8–3.6 (16H, m), 3.8–3.9 (6H, m), 4.42 (1H, d), 6.8–7.3 (8H, m).

Example 142

2-(4-(3,4-Dimethoxy-α-hydroxybenzyl)-1-piperidinyl)-2-(3,4-dimethoxyphenyl)-2-dodecylvaleronitrile hydrochloride
TLC Rf=0.18.
MS 636 (M+).
NMR 0.88 (3H, t), 1.1–3.6 (38H, m), 3.8–3.9 (12H, m), 4.3–4.4 (1H, m), 6.8–7.3 (6H, m).

Example 143

2-(3,4-Dimethoxyphenyl)-2-dodecyl-5-(4-phenyl-4-hydroxy-1-piperidinyl)valeronitrile hydrochloride
TLC Rf=0.45.

MS 562 (M+).
NMR (free base) 0.88 (3H, t), 1.0–2.9 (36H, m), 3.87 (3H, s), 3.93 (3H, s), 6.8–7.0 (3H, m), 7.2–7.6 (5H, m).

Example 144

5-(4-Benzhydryl-1-piperazinyl)-2-(3,4-dimethoxyphenyl)-2-dodecylvaleronitrile hydrochloride
TLC Rf=0.47.
MS 637 (M+).
NMR (free base) 0.88 (3H, t), 1.0–2.5 (36H, m), 3.84 (3H, s), 3.86 (3H, s), 4.20 (1H, s), 6.8–7.4 (13H, m).

Example 145

2-(3,4-Dimethoxyphenyl)-2-dodecyl-5-(4-(2,4,6-trimethylbenzyl)-1-piperidinyl)valeronitrile hydrochloride
TLC Rf=0.88.
MS 616 (M+).
NMR 0.88 (3H, t), 1.1–1.5 (22H, m), 1.8–3.5 (15H, m), 2.16, 2.18 (6H, 2s), 2.26, 2.29 (3H, 2s), 3.89, 3.90 (3H, 2s), 3.94, 3.96 (3H, s), 6.8–7.3 (5H, m).

Example 146

2-(3,4-Dimethoxyphenyl)-5-(4-(4-fluorobenzyl)-1-piperazinyl)-2-dodecylvaleronitrile hydrochloride
TLC Rf=0.34.
MS 579 (M+).
NMR 0.88 (3H, t), 1.1–3.4 (38H, m), 6.8–8.0 (7H, m).

Example 147

5-(4-Benzyl-1-piperazinyl)-2-(3,4-dimethoxyphenyl)-2-dodecylvaleronitrile hydrochloride
TLC Rf=0.39.
MS 561 (M+).
NMR 0.84 (3H, t), 1.1–3.4 (38H, m), 6.8–7.4 (8H, m).

Example 148

4-(3,4-Dimethoxyphenyl)-1-(4-(4-fluorobenzoyl)-1-piperidinyl)hexadecanenitrile hydrochloride
TLC Rf=0.79.
MS 567 (M+).
NMR (free base) 0.87 (3H, t), 1.1–3.9 (38H, m), 6.8–7.4 (8H, m).

Example 149

Methyl 2-(3,4-dimethoxyphenyl)-2-dodecyl-2-(3-(4-(4-fluorobenzoyl)-1-piperidinyl)-1-propyl)acetate hydrochloride
TLC Rf=0.61.
MS 625 (M+).
NMR (free base) 0.84 (3H, t), 1.2–1.5 (22H, m), 1.8–2.1 (8H, m), 2.9–3.1 (4H, m), 3.4–3.5 (2H, m), 3.6–3.8 (1H, m), 3.61 (3H, s), 3.76 (3H, s), 3.79 (3H, s), 6.9–7.0 (3H, m), 7.40 (2H, dd), 8.07 (2H, dd).

Example 150

2-(3,4-Dimethoxyphenyl)-2-dodecyl-2(3-(4-(4-fluorobenzoyl)-1-piperidinyl)-1-propyl)acetid acid hydrochloride
TLC Rf=0.24.
MS 612 (MH+).
NMR (D MSO-d6) 0.84 (3H, t), 1.2–1.5 (22H, m), 1.8–2.1 (8H, m), 2.9–3.1 (4H, m), 3.4–3.5 (2H, m), 3.6–3.8 (1H, m), 3.75 (3H, s), 3.78 (3H, s) 6.9–7.0 (3H, m), 7.32 (2H, dd), 8.12 (2H, dd).

Example 151

2-(3,4-Dimethoxyphenyl)-2-dodecyl-2-(3-(4-(4-fluorobenzoyl)-1-piperidinyl)-1-propyl)acetamide hydrochloride
TLC Rf=0.44.
MS 610 (M+).
NMR 0.87 (3H, t), 1.2–1.5 (22H, m), 1.8–2.1 (8H, m), 2.9–3.1 (4H, m), 3.4–3.5 (2H, m), 3.6–3.8 (1H, m), 3.82 (3H, s), 3.88 (3H, s), 6.9–7.0 (3H, m), 7.41 (2H, dd), 8.01 (2H, dd).

Example 152

2-(3,4-Dimethoxyphenyl)-7-(4-(α-hydroxy-4-fluorobenzoyl)-1-piperidinyl)-2-tridecylheptanenitrile hydrochloride
TLC Rf=0.67.
MS 580 (M+).
NMR 0.82 (3H, t), 1.1–3.4 (34H, m), 3.58 (3H, s), 3.86 (3H, s , 3.88 (3H, s), 6.9–8.0 (7H, m).

Example 153

N-(3-(4-(4-Fluorobenzoyl)-1-propyl)-N-methyl 4-cyano-4-(3,4-dimethoxyphenyl)hexadecylamine hydrochloride
TLC Rf=0.32.
MS 582 (M+).
NMR 0.87 (3H, t), 1.1–3.4 (34H, m), 3.58 (3H, s), 3.86 (3H, s , 3.88 (3H, s), 4.25 (1H, d), 6.9–8.0 (7H, m).

Example 154

4-(5H-Dibenzo[a,d]cyclohepten-5-ylidene)-1-hexylpiperidine hydrochloride

A solution of 273 mg (1 mmol) of 4-(5H-dibenzo[a,d]cyclo-hepten-5-ylidene)-1-hexylpiperidine, 165 mg (1 mmol) of 1-bromohexane, 745 mg (5 mmols) of sodium iodide and 414 mg (3 mmols) of potassium carbonate in 20 ml of methyl isobutyl ketone was stirred and refluxed at 120° C. overnight on an oil bath. After the reaction, the mixture was washed by adding 20 ml of water thereto. Then the organic phase was separated and the solvent was distilled off under reduced pressure. After purifying by silica gel column chromatography (eluent: methanol/chloroform, 1/100–1/50), the product was converted into the hydrochloride with an equimolar hydrogen chloride/dioxane solution.

Amount yielded 180 mg.
Yield 46%.
TLC Rf=0.68.
MS 357 (M+).
NMR 0.83 (3H, t), 1.2–1.4 (6H, m), 1.7–1.9 (2H, m), 2.31 (2H, dd), 2.53 (2H, d), 2.7–2.8 (2H, m), 3.14 (2H, dd), 3.38 (2H, dd), 3.38 (2H, d), 6.92 (2H, s), 7.2–7.4 (8H, m).

The procedures of the following examples were conducted in a manner similar to that of Example 154.

Example 155

4-(5H-Dibenzo[a,d]cyclohepten-5-ylidene)-1-octylpiperidine hydrochloride
Amount yielded 300 mg.
Yield 72%.
TLC Rf=0.71.
MS 385 (M+).
NMR 0.85 (3H, t), 1.2–1.4 (10H, m), 1.7–2.0 (2H, m), 2.30 (2H, dd), 2.53 (2H, d), 2.7–2.9 (2H, m), 3.13 (2H, dd), 3.38 (2H, d), 6.90 (2H, s), 7.1–7.4 (8H, m).

Example 156

1-Decyl-4-(5H-dibenzo[a,d]cyclohepten-5-ylidene)-piperidine hydrochloride
Amount yielded 300 mg.
Yield 67%.
TLC Rf=0.75.
MS 413 (M+).
NMR 0.85 (3H, t), 1.2-1.4 (14H, m), 1.7-1.9 (2H, m), 2.33 (2H, dd), 2.54 (2H, d), 2.7-2.8 (2H, m), 3.15 (2H, dd), 3.39 (2H, d), 6.92 (2H, s), 7.1-7.4 (8H, m).

Example 157

4-(5H-Dibenzo[a,d]cyclohepten-5-ylidene)-1-dodecylpiperidine hydrochloride
Amount yielded 1.10 g.
Yield 92%.
TLC Rf=0.78.
MS 441 (M+).
NMR 0.85 (3H, t), 1.1-1.5 (18H, m), 1.7-1.9 (2H, m), 2.32 (2H, dd), 2.54 (2H, d), 2.7-2.8 (2H, m), 3.12 (2H, dd), 3.36 (2H, d), 6.93 (2H, s), 7.1-7.4 (8H, m).

Example 158

4-(5H-Dibenzo[a,d]cyclohepten-5-ylidene)-1-tetradecylpiperidine hydrochloride
Amount yielded 1.20 g.
Yield 95%.
TLC Rf=0.78.
MS 469 (M+).
NMR 0.82 (3H, t), 1.1-1.5 (22H, m), 1.7-1.9 (2H, m), 2.33 (2H, dd), 2.55 (2H, d), 2.7-2.8 (2H, m), 3.15 (2H, dd), 3.40 (2H, d), 6.92 (2H, s), 7.1-7.4 (8H, m).

Example 159

4-(5H-Dibenzo[a,d]cyclohepten-5-ylidene)-1-hexadecylpiperidine hydrochloride
Amount yielded 1.18 g.
Yield 88%.
TLC Rf=0.80.
MS 497 (M+).
NMR 0.80 (3H, t), 1.1-1.6 (26H, m), 1.7-1.9 (2H, m), 2.33 (2H, dd), 2.58 (2H, d), 2.7-2.8 (2H, m), 3.20 (2H, dd), 3.40 (2H, d), 6.88 (2H, s), 7.1-7.4 (8H, m).

Example 160

1-Cyclohexylmethyl-4-(5H-dibenzo[a,d]cyclohepten-5-ylidene)-piperidine hydrochloride
Amount yielded 520 mg.
Yield 51%.
TLC Rf=0.75.
MS 369 (M+).
NMR 0.8-2.1 (11H, m), 2.42 (2H, dd), 2.65 (2H, d), 2.78 (2H, d), 3.20 (2H, dd), 3.42 (2H, d), 6.91 (2H, s), 7.1-7.4 (8H, m).

Example 161

1-Cyclohexyl-2-(4-(5H-dibenzo[a,d]cyclohepten-5-ylidene)-1-piperidinyl)ethane hydrochloride
Amount yielded 780 mg.
Yield 74%.
TLC Rf=0.75.
MS 383 (M+).
NMR 0.8-2.1 (13H, m), 2.45 (2H, dd), 2.67 (2H, d), 2.7-2.9 (2H, m), 3.0 (2H, dd), 3.48 (2H, d), 6.94 (2H, s), 7.1-7.4 (8H, m).

Example 162

1-Cyclohexyl-3-(4-(5H-dibenzo[a,d]cyclohepten-5-ylidene)-1-piperidinyl)propane hydrochloride
Amount yielded 1.02 g.
Yield 94%.
TLC Rf=0.77.
MS 397 (M+).
NMR 0.8-2.1 (15H, m), 2.47 (2H, dd), 2.68 (2H, d), 2.7-2.9 (2H, m), 3.0 (2H, dd), 3.49 (2H, d), 6.94 (2H, s), 7.1-7.4 (8H, m).

Example 163

1-Cyclohexyl-4-(4-(5H-dibenzo[a,d]cyclohepten-5-ylidene)-1-piperidinyl)butane hydrochloride
Amount yielded 815 mg.
Yield 72%.
TLC Rf=0.78.
MS 411 (M+).
NMR 0.8-2.1 (17H, m), 2.28 (2H, dd), 2.52 (2H, d), 2.7-2.9 (2H, m), 3.08 (2H, dd), 3.35 (2H, d), 6.92 (2H, s), 7.1-7.4 (8H, m).

Example 164

1-Cyclohexyl-5-(4-(5H-dibenzo[a,d]cyclohepten-5-ylidene)-1-piperidinyl)pentane hydrochloride
Amount yielded 750 mg.
Yield 65%.
TLC Rf=0.80.
MS 411 (M+).
NMR 0.8-2.1 (19H, m), 2.25 (2H, dd), 2.68 (2H, d), 2.7-2.9 (2H, m), 3.12 (2H, dd), 3.38 (2H, d), 6.92 (2H, s), 7.1-7.4 (8H, m).

Example 165

1-Benzyl-4-(5H-dibenzo[a,d]cyclohepten-5-ylidene)-piperidine hydrochloride
Amount yielded 320 mg.
Yield 80%.
TLC Rf=0.42.
MS 363 (M+).
NMR 2.28 (2H, dd), 2.52 (2H, d), 3.14 (2H, dd), 3.31 (2H, d), 4.01 (2H, d), 6.90 (2H, s), 7.1-7.6 (13H, m).

Example 166

2-(4-(5H-Dibenzo[a,d]cyclohepten-5-ylidene)-1-piperidinyl)-1-phenylethane hydrochloride
Amount yielded 310 mg.
Yield 75%.
TLC Rf=0.45.
MS 377 (M+).
NMR 2.28 (2H, dd), 2.51 (2H, d), 3.0-3.3 (6H, m), 3.47 (2H, d), 6.90 (2H, s), 7.1-7.4 (13H, m).

Example 167

3-(4-(5H-Dibenzo[a d]cyclohepten-5-ylidene)-1-piperidinyl)-1-phenylpropane hydrochloride
Amount yielded 330 mg.
Yield 77%.
TLC Rf=0.50.
MS 391 (M+).
NMR 2.1-2.4 (4H, m), 2.51 (2H, d), 2.65 (2H, t), 2.7-2.9 (2H, m), 3.12 (2H, dd), 3.38 (2H, d), 6.90 (2H, s), 7.1-7.4 (13H, m).

Example 168

(4-(5H-Dibenzo[a,d]cyclohepten-5-ylidene)-1-piperidinyl)-1-phenylbutane hydrochloride Amount yielded 180 mg.
Yield 41%.
TLC Rf=0.50.
MS 405 (M+).
NMR 1.4–1.9 (4H, m), 2.28 (2H, dd), 2.52 (2H, d), 2.61 (2H, t), 2.7–2.8 (2H, m), 3.12 (2H, dd), 3.35 (2H, d), 6.90 (2H, s), 7.1–7.4 (13H, m).

Example 169

5-(4-(5H-Dibenzo[a,d]cyclohepten-5-ylidene)-1-piperidinyl)-1-phenylpentane hydrochloride
Amount yielded 110 mg.
Yield 24%.
TLC Rf=0.55.
MS 419 (M+).
NMR 1.2–1.9 (6H, m), 2.25 (2H, dd), 2.52 (2H, d), 2.60 (2H, t), 2.7–2.8 (2H, m), 3.08 (2H, dd), 3.35 (2H, d), 6.90 (2H, s), 7.1–7.4 (13H, m).

Example 170

6-(4-(5H-Dibenzo[a,d]cyclohepten-5-ylidene)-1-piperidinyl)-1-phenylhexane hydrochloride
Amount yielded 315 mg.
Yield 67%.
TLC Rf=0.56.
MS 433 (M+).
NMR 1.1–1.9 (8H, m), 2.26 (2H, dd), 2.56 (2H, d), 2.61 (2H, t), 2.7–2.8 (2H, m), 3.10 (2H, dd), 3.35 (2H, d), 6.91 (2H, s), 7.1–7.4 (13H, m).

Example 171

7-(4-(5H-Dibenzo[a,d]cyclohepten-5-ylidene)-1-piperidinyl)-1-phenylheptane hydrochloride
Amount yielded 267 mg.
Yield 55%.
TLC Rf=0.56.
MS 447 (M+).
NMR 1.1–1.9 (10H, m), 2.25 (2H, dd), 2.55 (2H, d), 2.65 (2H, t), 2.7–2.8 (2H, m), 3.07 (2H, dd), 3.32 (2H, d), 6.90 (2H, s), 7.1–7.4 (13H, m).

Example 172

2-(4-(5H-Dibenzo[a,d]cyclohepten-5-ylidene)-1-piperidinyl)-1-phenoxyethane hydrochloride
Amount yielded 1.95 g.
Yield 55%.
TLC Rf=0.56.
MS 393 (M+).
NMR (fee base) 2.1–2.5 (2H, m), 2.58 (2H, t), 2.6–2.7 (2H, m), 4.05 (2H, t), 6.89 (2H, d), 6.92 (2H, s), 7.1–7.4 (11H, m).

Example 173

3-(4-(5H-Dibenzo[a,d]cyclohepten-5-ylidene)-1-piperidinyl)-1-phenoxypropane hydrochloride
Amount yielded 2.15 g.
Yield 48%.
TLC Rf=0.58.
MS 407 (M+).
NMR (free base) 1.97 (2H, tt), 2.1–2.5 (6H, m), 2.54 (2H, t), 2.6–2.7 (2H, m), 3.97 (2H, dd), 6.86 (2H, d), 6.90 (2H, s), 7.1–7.4 (11H, m).

Example 174

4-(4-(5H-Dibenzo[a,d]cyclohepten-5-ylidene)-1-piperidinyl)-1-phenoxybutane hydrochloride
Amount yielded 1.18 g.
Yield 86%.
TLC Rf=0.61.
MS 421 (M+).
NMR (free base) 1.8–2.7 (14H, m), 3.96 (2H, t), 6.87 (2H, d), 6.90 (2H, s), 7.1–7.4 (11H, m).

Example 175

2-(4-(5H-dibenzo[a,d]cyclohepten-5-ylidene)-1-piperidinyl)-1-phenylthioethane hydrochloride
Amount yielded 0.97 g.
Yield 87%.
TLC Rf=0.55.
MS 409 (M+).
NMR (free base) 2.0–2.6 (10H, m), 2.78 (2H, t), 6.86 (2H, s), 7.1–7.4 (11H, m).

Example 176

3-(4-(5H-Dibenzo[a,d]cyclohepten-5-ylidene)-1-piperidinyl)-1-phenylthiopropane hydrochloride
Amount yielded 0.85 g.
Yield 74%.
TLC Rf=0.62.
MS 423 (M+).
NMR (free base) 1.73 (2H, tt), 2.0–2.6 (10H, m), 2.80 (2H, t), 6.88 (2H, d), 7.1–7.4 (11H, m).

Example 177

4-(4-(5H-Dibenzo[a,d]cyclohepten-5-ylidene)-1-piperidinyl)-1-phenylthiobutane hydrochloride
Amount yielded 0.85 g.
Yield 72%.
TLC Rf=0.62.
MS 437 (M+).
NMR (free base) 1.6–2.6 (14H, m), 2.80 (2H, t), 6.88 (2H, d), 7.1–7.4 (11H, m).

Example 178

4-(5H-Dibenzo[a,d]cyclohepten-5-ylidene)-1-(2-(2-nitrobenzene-sulfonyl)aminoethyl)piperidine hydrochloride
TLC Rf=0.72.
MS 502 (M+).

Example 179

1-(2-(2-Aminobenzenesulfonyl)aminoethyl)-4-(5H-dibenzo[a,d]-cyclohepten-5-ylidene)piperidine hydrochloride
TLC Rf=0.51.
MS 472 (M+).

Example 180

4-(5H-Dibenzo[a,d]cyclohepten-5-ylidene)-1-(2-(2-ethoxycarbonyl-benzenesulfonyl)aminoethyl)piperidine hydrochloride
TLC Rf=0.68.
MS 544 (M+).

Example 181

3-(2-((4-(5H-Dibenzo[a,d]cyclohepten-5-ylidene)-1-piperidinyl)-ethyl)-2,4(1H,3H)quinazolinedione hydrochloride
TLC Rf=0.85.
MS 462 (M+).

Example 182

5,6-Benzo-2,4-diazo(2-(4-(5H-dibenzo[a,d]cyclohepten-5-ylidene)-1-piperidinyl)ethyl)tetrahydrothiopyran hydrochloride
TLC Rf=0.91.

MS 498 (M+).

Example 183

2-(4-(5H-Dibenzo[a,d]cyclohepten-5-ylidene)-1-piperidinyl)-1-(3,4-dimethoxyphenyl)ethane hydrochloride
TLC Rf=0.78.
MS 450 (M+).

Example 184

3-(4-(5H-Dibenzo[a,d]cyclohepten-5-ylidene)-1-piperidinyl)-propyl-4-fluorophenylsulfoxide hydrochloride
TLC Rf=0.78.
MS 457 (M+).

Example 185

3-(4-(5H-Dibenzo[a,d]cyclohepten-5-ylidene)-1-piperidinyl)-propyl-4 fluorophenylsulfone hydrochloride
TLC Rf=0.62.
MS 473 (M+).

Example 186

4-(5H-Dibenzo[a,d]cyclohepten-5-ylidene)-1-(3-(2-aminophenylthio)-1-propyl)piperidine hydrochloride
TLC Rf=0.84.
MS 439 (M+).

Example 187

4-(5H-Dibenzo[a,d]cyclohepten-5-ylidene)-1-(1-(2-benzoylamino)-ethyl)piperidine hydrochloride
TLC Rf=0.84.
MS 420 (M+).

Example 188

4-(5H-Dibenzo[a d]cyclohepten-5-ylidene)-1-(1-(2-N-phenyl-carbamoylamino)ethyl)piperidine hydrochloride
TLC Rf=0.55.
MS 435 (M+).

Example 189

1-(3-(2-Cinnamoylaminophenylthio)-1-propyl)-4-(5H-dibenzo[a,d]-cyclohepten-5-ylidene)piperidine hydrochloride
TLC Rf=0.66.
MS 568 (M+).
NMR (free base) 1.74 (2H, tt), 2.0–2.6 (8H, m), 2.80 (2H, t), 6.59 (1H, d), 6.88 (2H, s), 7.0–7.6 (16H, m), 7.75 (1H, d), 8.5 (1H, d), 8.68 (1H, bs).

Example 190

1-Cinnamyl-4-(5H-dibenzo[a,d]cyclohepten-5-ylidene)-piperidine hydrochloride
TLC Rf=0.84.
MS 389 (M+).
NMR (free base) 2.1–2.7 (8H, m), 3.15 (2H, d), 6.25 (1H, td), 6.47 (1H, d), 6.90 (2H, s), 7.1–7.4 (13H, m).

Example 191

5-(4-(5H-Dibenzo[a,d]cyclohepten-5-ylidene)-1-piperidinyl)-2-(3,4,5-trimethoxyphenyl)-2-isopropylvaleronitrile hydrochloride
TLC Rf=0.80.
MS 563 (M+).

Example 192

2-(3-(4-(5H-Dibenzo[a,d]cyclohepten-5-ylidene)-1-piperidinyl)-1-propyl)-2-phenyl-1,3-dithiane-1,1,3,3-tetroxide hydrochloride
TLC Rf=0.48.
MS 573 (M+).

Example 193

2-(3,4-Dimethoxyphenyl)-2-(3-(4-(5H-dibenzo[a,d]cyclohepten-5-ylidene)-1-piperidinyl)-1-propyl)-1,3-dithiane-1,1,3,3-tetroxide hydrochloride
TLC Rf=0.48.
MS 573 (M+).

Example 194

5-(4-(5H-Dibenzo[a,d]cyclohepten-5-ylidene)-1-piperidinyl)-2-(3,4-dichlorophenyl)-2-isopropylvaleronitrile hydrochloride
TLC Rf=0.94.
MS 540 (M+).

Example 195

2-(3-Benzoylphenyl)-5-(4-(5H-dibenzo[a,d]cyclohepten-5-ylidene)-1-piperidinyl)-2-methylvaleronitrile hydrochloride
TLC Rf=0.88.
MS 548 (M+).

Example 196

5-(4-(5H-Dibenzo[a,d]cyclohepten-5-ylidene)-1-piperidinyl)-2,2-diphenylvaleronitrile hydrochloride
TLC Rf=0.74.
MS 506 (M+).

Example 197

4-(4-(5H-Dibenzo[a,d]cyclohepten-5-ylidene)-1-piperidinyl)-3',4'-dimethoxybutyrophenone hydrochloride
TLC Rf=0.61.
MS 479 (M+).

Example 198

6-(4-(5H-Dibenzo[a,d]cyclohepten-5-ylidene)-1-piperidinyl)-2-phenylhexanenitrile hydrochloride
TLC Rf=0.86.
MS 430 (M+).

Example 199

6-(4-(5H-Dibenzo[a,d]cyclohepten-5-ylidene)-1-piperidinyl)-2-isopropyl-2-phenylhexanenitrile hydrochloride
TLC Rf=0.88.
MS 472 (M+).

Example 200

6-(4-(5H-Dibenzo[a,d]cyclohepten-5-ylidene)-1-piperidinyl)-2-(3,4-dimethoxyphenyl)-2-isopropylhexanenitrile hydrochloride
TLC Rf=0.81.
MS 546 (M+).

Example 201

7-(4-(5H-Dibenzo[a,d]cyclohepten-5-ylidene)-1-piperidinyl)-2-phenylheptanenitrile hydrochloride
TLC Rf=0.84.
MS 444 (M+).

Example 202

7-(4-(5H-Dibenzo[a,d]cyclohepten-5-ylidene)-1-piperidinyl)-2-isopropyl-2-phenylheptanenitrile hydrochloride
TLC Rf=0.84.
MS 486 (M+).

Example 203

7-(4-(5H-Dibenzo[a,d]cyclohepten-5-ylidene)-1-piperidinyl)-2-(3,4-dimethoxyphenyl)-2-isopropylheptanenitrile hydrochloride
TLC Rf=0.86.
MS 560 (M+).

Example 204

2-(3-Chloropropyl)-5-(4-(5H-dibenzo[a,d]cyclohepten-5-ylidene)-1-piperidinyl)-2-phenylvaleronitrile hydrochloride
TLC Rf=0.92.
MS 506 (M+).

Example 205

5-(4-(5H-Dibenzo[a,d]cyclohepten-5-ylidene)-1-piperidinyl)-2-phenyl-2-phenylthiovaleronitrile hydrochloride
TLC Rf=0.81.
MS 538 (M+).

Example 206

5-(4-(5H-Dibenzo[a,d]cyclohepten-5-ylidene)-1-piperidinyl)-2-(3,4-dimethoxyphenyl)-2-phenylthiovaleronitrile hydrochloride
TLC Rf=0.91.
MS 598 (M+).

Example 207

5-(4-(5H-Dibenzo[a,d]cyclohepten-5-ylidene)-1-piperidinyl)-2-(1-naphthyl)valeronitrile hydrochloride
TLC Rf=0.85.
MS 580 (M+).

Example 208

5-(4-(5H-Dibenzo[a,d]cyclohepten-5-ylidene)-1-piperidinyl)-2-(1-naphthyl)-2 isopropylvaleronitrile hydrochloride
TLC Rf=0.90.
MS 522 (M+).

Example 209

5-(4-(5H-Dibenzo[a,d]cyclohepten-5-ylidene)-1-piperidinyl)-2-(2-naphthyl)valeronitrile hydrochloride
TLC Rf=0.85.
MS 480 (M+).

Example 210

5-(4-(5H-Dibenzo[a,d]cyclohepten-5-ylidene)-1-piperidinyl)-2-(2-naphthyl)-2-isopropylvaleronitrile hydrochloride
TLC Rf=0.87.
MS 522 (M+).

Example 211

5-(4-(5H-Dibenzo[a,d]cyclohepten-5-ylidene)-1-piperidinyl)-2-(3-trifluoromethylphenyl)valeronitrile hydrochloride
TLC Rf=0.72.
MS 498 (M+).

Example 212

5-(4-(5H-Dibenzo[a,d]cyclohepten-5-ylidene)-1-piperidinyl)-2-isopropyl-2-(3-trifluoromethylphenyl)-valeronitrile hydrochloride
TLC Rf=0.75.
MS 540 (M+).

Example 213

8-(4-(5H-Dibenzo[a,d]cyclohepten-5-ylidene)-1-piperidinyl)-2-phenyloctanenitrile hydrochloride
TLC Rf=0.84.
MS 472 (M+).

Example 214

8-(4-(5H-Dibenzo[a,d]cyclohepten-5-ylidene)-1-piperidinyl)-2-isopropyl-2-phenyloctanenitrile hydrochloride
TLC Rf=0.88.
MS 514 (M+).

Example 215

8-(4-(5H-Dibenzo[a,d]cyclohepten-5-ylidene)-1-piperidinyl)-2-(3,4-dimethoxyphenyl)-2-isopropyloctanenitrile hydrochloride
TLC Rf=0.82.
MS 574 (M+).

Example 216

1-(3-(4-(5H-Dibenzo[a,d]cyclohepten-5-ylidene)-1-piperidinyl)-1-propyl)-1-indanenitrile hydrochloride
TLC Rf=0.90.
MS 456 (M+).

Example 217

1-(3-(4-(5H-Dibenzo[a,d]cyclohepten-5-ylidene)-1-piperidinyl)-1-propyl)-5,6-dimethoxy-1-indanenitrile hydrochloride
TLC Rf=0.85.
MS 516 (M+).

Example 218

5-(4-(5H-Dibenzo[a,d]cyclohepten-5-ylidene)-1-piperidinyl)-2-(1-methylpyrrol-2-yl)valeronitrile hydrochloride
TLC Rf=0.61.
MS 433 (M+).

Example 219

5-(4-(5H-Dibenzo[a,d]cyclohepten-5-ylidene)-1-piperidinyl)-2-isopropyl-2-(1-methylpyrrol-2-yl)valeronitrile hydrochloride
TLC Rf=0.71.
MS 475 (M+).

Example 220

5-(4-(5H-Dibenzo[a,d]cyclohepten-5-ylidene)-1-piperidinyl)-2-isopropyl-2-(pyrrol-2-yl)valeronitrile hydrochloride
TLC Rf=0.55.
MS 461 (M+).

Example 221

5-(4-(5H-Dibenzo[a,d]cyclohepten-5-ylidene)-1-piperidinyl)-2-(3-α-hydroxybenzyl)phenyl)-2-methylvaleronitrile hydrochloride
TLC Rf=0.51.
MS 550 (M+).

Example 222

2-(3-Benzoylphenyl)-6-(4-(5H-Dibenzo[a,d]cyclohepten-5-ylidene)-1-piperidinyl)-2-methylhexanenitrile hydrochloride
  TLC Rf=0.88.
  MS 562 (M+).

Example 223

6-{4-(5H-Dibenzo[a,d]cyclohepten-5-ylidene)-1-piperidinyl)-2-(3-(α-hydroxybenzyl)phenyl-2-methylhexanenitrile hydrochloride
  TLC Rf=0.52.
  MS 564 (M+).

Example 224

2-(3-Benzoylphenyl)-7-(4-(5H-Dibenzo[a,d]cyclohepten-5-ylidene)-1-piperidinyl)-2-methylheptanenitrile hydrochloride
  TLC Rf=0.91.
  MS 576 (M+).

Example 225

7-(4-(5H-Dibenzo[a,d]cyclohepten-5-ylidene)-1-piperidinyl)-2-(3-(α-hydroxybenzyl)phenyl-2-methylheptanenitrile hydrochloride
  TLC Rf=0.52.
  MS 578 (M+).

Example 226

2-(3-Benzoylphenyl)-8-(4-(5H-Dibenzo[a,d]cyclohepten-5-ylidene)-1-piperidinyl)-2-methyloctanenitrile hydrochloride
  TLC Rf=0.90.
  MS 590 (M+).

Example 227

8-(4-(5H-Dibenzo[a,d]cyclohepten-5-ylidene)-1-piperidinyl)-2-(3-(α-hydroxybenzyl)phenyl-2-methyloctanenitrile hydrochloride
  TLC Rf=0.61.
  MS 592 (M+).

Example 228

5-(4-(5H-Dibenzo[a,d]cyclohepten-5-ylidene)-1-piperidinyl)-2-methyl-2-phenylvaleronitrile hydrochloride
  TLC Rf=0.91.
  MS 544 (M+).

Example 229

5-(4-(5H-Dibenzo[a,d]cyclohepten-5-ylidene)-1-piperidinyl)-2-(3,4-dimethoxyphenyl)-2-methylvaleronitrile hydrochloride
  TLC Rf=0.85.
  MS 504 (M+).

Example 230

5-(4-(5H-Dibenzo[a,d]cyclohepten-5-ylidene)-1-piperidinyl)-2-ethyl-2-phenylvaleronitrile hydrochloride
  TLC Rf=0.92.
  MS 458 (M+).

Example 231

5-(4-(5H-Dibenzo[a,d]cyclohepten-5-ylidene)-1-piperidinyl)-2-(3,4-dimethoxyphenyl)-2-ethylvaleronitrile hydrochloride
  TLC Rf=0.90.
  MS 518 (M+).

Example 232

5-(4-(5H-Dibenzo[a,d]cyclohepten-5-ylidene)-1-piperidinyl)-2-propyl-2-phenylvaleronitrile hydrochloride
  TLC Rf=0.93.
  MS 472 (M+).

Example 233

5-(4-(5H-Dibenzo[a,d]cyclohepten-5-ylidene)-1-piperidinyl)-2-(3,4-dimethoxyphenyl)-2-propylvaleronitrile hydrochloride
  TLC Rf=0.91.
  MS 532 (M+).

Example 234

2-Butyl-5-(4-(5H-Dibenzo[a,d]cyclohepten-5-ylidene)-1-piperidinyl)-2-phenylvaleronitrile hydrochloride
  TLC Rf=0.95.
  MS 486 (M+).

Example 235

2Butyl-5-(4-(5H-Dibenzo[a,d]cyclohepten-5-ylidene)-1-piperidinyl)-2-(3,4-dimethoxyphenyl)valeronitrile hydrochloride
  TLC Rf=0.90.
  MS 546 (M+).

Example 236

5-(4-(5H-Dibenzo[a,d]cyclohepten-5-ylidene)-1-piperidinyl)-2-pentyl-2-phenylvaleronitrile hydrochloride
  TLC Rf=0.95.
  MS 500 (M+).

Example 237

5-(4-(5H-Dibenzo[a,d]cyclohepten-5-ylidene)-1-piperidinyl)-2-(3,4-dimethoxyphenyl)-2-pentylvaleronitrile hydrochloride
  TLC Rf=0.92.
  MS 560 (M+).

Example 238

5-(4-(5H-Dibenzo[a,d]cyclohepten-5-ylidene)-1-piperidinyl)-2-hexyl-2-phenylvaleronitrile hydrochloride
  TLC Rf=0.95.
  MS 514 (M+).

Example 239

5-(4-(5H-Dibenzo[a,d]cyclohepten-5-ylidene)-1-piperidinyl)-2-(3,4-dimethoxyphenyl)-2-hexylvaleronitrile hydrochloride
  TLC Rf=0.92.
  MS 574 (M+).

Example 240

5-(4-(5H-Dibenzo[a,d]cyclohepten-5-ylidene)-1-piperidinyl)-2-heptyl-2-phenylvaleronitrile hydrochloride
  TLC Rf=0.95.
  MS 528 (M+).

Example 241

5-(4-(5H-Dibenzo[a,d]cyclohepten-5-ylidene)-1-piperidinyl)-2-(3,4-dimethoxyphenyl)-2-heptylvaleronitrile hydrochloride
 TLC Rf=0.91.
 MS 588 (M+).

Example 242

5-(4-(5H-Dibenzo[a,d]cyclohepten-5-ylidene)-1-piperidinyl)-2-octyl-2-phenylvaleronitrile hydrochloride
 TLC Rf=0.94.
 MS 543 (M+).

Example 243

5-(4-(5H-Dibenzo[a,d]cyclohepten-5-ylidene)-1-piperidinyl)-2-(3,4-dimethoxypheny)-2-octylvaleronitrile hydrochloride
 TLC Rf=0.94.
 MS 602 (M+).

Example 244

5-(4-(5H-Dibenzo[a,d]cyclohepten-5-ylidene)-1-piperidinyl)-2-nonyl-2-phenylvaleronitrile hydrochloride
 TLC Rf=0.95.
 MS 556 (M+).

Example 245

5-(4-(5H-Dibenzo[a,d]cyclohepten-5-ylidene)-1-piperidinyl)-2-(3,4-dimethoxyphenyl)-2-nonylvaleronitrile hydrochloride
 TLC Rf=0.93.
 MS 616 (M+).

Example 246

2-Decyl-5-(4-(5H Dibenzo[a,d]cyclohepten-5-ylidene)-1-piperidinyl)-2-phenylvaleronitrile hydrochloride
 TLC Rf=0.95.
 MS 570 (M+).

Example 247

2-Decyl-5-(4-(5H-Dibenzo[a,d]cyclohepten-5-ylidene)-1-piperidinyl)-2-(3,4-dimethoxyphenyl)valeronitrile hydrochloride
 TLC Rf=0.94.
 MS 630 (M+).

Example 248

5-(4-(5H-Dibenzo[a,d]cyclohepten-5-ylidene)-1-piperidinyl}-acetophenone hydrochloride
 TLC Rf=0.71.
 MS 391 (M+).

Example 249

2-(4-(5H-Dibenzo[a,d]cyclohepten-5-ylidene)-1-piperidinyl)-1-hydroxy-1-phenylethane hydrochloride
 TLC Rf=0.36.
 MS 393 (M+).

Example 250

3-(4-(5H-Dibenzo[a,d]cyclohepten-5-ylidene)-1-piperidinyl)-propiophenone hydrochloride
 TLC Rf=0.74.
 MS 405 (M+).

Example 251

3-(4-(5H-Dibenzo[a,d]cyclohepten-5-ylidene)-1-piperidinyl)-1-hydroxy-1-phenylpropane hydrochloride
 TLC Rf=0.35.
 MS 407 (M+).

Example 252

3-(4-(5H-Dibenzo[a,d]cyclohepten-5-ylidene)-1-piperidinyl)-butyrophenone hydrochloride
 TLC. Rf=0.75.
 MS 419 (M+).

Example 253

4-(4-(5H-Dibenzo[a,d]cyclohepten-5-ylidene)-1-piperidinyl)-1-hydroxy-1-phenylbutane hydrochloride
 TLC Rf=0.39.
 MS 421 (M+).

Example 254

5-(4-(5H-Dibenzo[a,d]cyclohepten-5-ylidene)-1-piperidinyl)-valerophenone hydrochloride
 TLC Rf=0.76.
 MS 433 (M+).

Example 255

5-(5H-Dibenzo[a,d]cyclohepten-5-ylidene)-1-piperidinyl)-1-hydroxy-1-phenylpentane hydrochloride
 TLC Rf=0.78.
 MS 447 (M+).

Example 256

2-(4-(5H-Dibenzo[a,d]cyclohepten-5-ylidene)-1-piperidinyl)-4'-fluoroacetophenone hydrochloride
 TLC Rf=0.80.
 MS 409 (M+).

Example 257

2-(4-(5H-Dibenzo[a,d]cyclohepten-5-ylidene)-1-piperidinyl)-1-hydroxy-1-(4-fluorophenyl)ethane hydrochloride
 TLC Rf=0.44.
 MS 411 (M+).

Example 258

3-(4-(5H-Dibenzo[a,d]cyclohepten-5-ylidene)-1-piperidinyl)-4'-fluoropropiophenone hydrochloride
 TLC Rf=0.80.
 MS 423 (M+).

Example 259

3-(4-(5H-Dibenzo[a,d]cyclohepten-5-ylidene)-1-piperidinyl)-1-hydroxy-1-(4-fluorophenyl)propane hydrochloride
 TLC Rf=0.44.
 MS 425 (M+).

Example 260

4-(4-(5H-Dibenzo[a,d]cyclohepten-5-ylidene)-1-piperidinyl)-1-hydroxy-1-(4-fluorophenyl)butane hydrochloride
 TLC Rf=0.45.
 MS 439 (M+).

Example 261

5-(4-(5H-Dibenzo[a,d]cyclohepten-5-ylidene)-1-piperidinyl)-4'-fluorovalerophenone hydrochloride
 TLC Rf=0.84.

MS 451 (M+).

Example 262

5-(4-(5H-Dibenzo[a,d]cyclohepten-5-ylidene)-1-piperidinyl)-1-hydroxy-1-(4-fluorophenyl)pentane hydrochloride
TLC Rf=0.51.
MS 453 (M+).

Example 263

4-(5H-Dibenzo[a,d]cyclohepten-5-ylidene)-1-(2-fluorobenzyl)-piperidine hydrochloride
TLC Rf=0.75.
MS 381 (M+).

Example 264

4-(5H-Dibenzo[a,d]cyclohepten-5-ylidene)-1-(3-fluorobenzyl)-piperidine hydrochloride
TLC Rf=0.79.
MS 381 (M+).

Example 265

4-(5H-Dibenzo[a,d]cyclohepten-5-ylidene)-1-(4-fluorobenzyl)-piperidine hydrochloride
TLC Rf=0.61.
MS 381 (M+).

Example 266

4-(5H-Dibenzo[a,d]cyclohepten-5-ylidene)-1-(2-trifluoromethylbenzyl)piperidine hydrochloride
TLC Rf=0.83.
MS 431 (M+).

Example 267

4-(5H-Dibenzo[a,d]cyclohepten-5-ylidene)-1-(3-trifluoromethylbenzyl)piperidine hydrochloride
TLC Rf=0.82.
MS 431 (M+).

Example 268

5-(4-(5H-Dibenzo[a,d]cyclohepten-5-ylidene)-1-piperidine hydrochloride
TLC Rf=0.79.
MS 431 (M+).

Example 269

4-(5H-Dibenzo[a,d]cyclohepten-5-ylidene)-1-(2-methoxybenzyl)piperidine hydrochloride
TLC Rf=0.61.
MS 393 (M+).

Example 270

4-(5H-Dibenzo[a,d]cyclohepten-5-ylidene)-1-(3-methoxybenzyl)piperidine hydrochloride
TLC Rf=0.61.
MS 393 (M+).

Example 271

4-(5H-Dibenzo[a,d]cyclohepten-5-ylidene)-1-(4-methoxybenzyl)piperidine hydrochloride
TLC Rf=0.52.
MS 393 (M+).

Example 272

4-(5H-Dibenzo[a,d]cyclohepten-5-ylidene)-1-pentafluorobenzyl-piperidine hydrochloride
TLC Rf=0.80.
MS 453 (M+).

Example 273

5-(4-(5H-Dibenzo[a,d]cyclohepten-5-ylidene)-1-piperidinyl)-2-phenylvaleronitrile hydrochloride
TLC Rf=0.86.
MS 440 (M+).

Example 274

5-(4-(5H-Dibenzo[a,d]cyclohepten-5-ylidene)-1-piperidinyl)-2-isopropyl-2-phenylvaleronitrile hydrochloride
TLC Rf=0.82.
MS 488 (M+).

Example 275

5-(4-(5H-Dibenzo[a,d]cyclohepten-5-ylidene)-1-piperidinyl)-2-(3,4-dimethoxyphenyl)valeronitrile hydrochloride
TLC Rf=0.75.
MS 500 (M+).

Example 276

2-(3-(4-(5H-Dibenzo[a,d]cyclohepten-5-ylidene)-1-piperidinyl)-1-propyl)-2 (4-fluorophenyl)-1,3-dioxolane hydrochloride
TLC Rf=0.68.
MS 481 (M+).

Example 277

4-(4-(5H-Dibenzo[a,d]cyclohepten-5-ylidene)-1-piperidinyl)-4'-fluorobutyrophenone hydrochloride
TLC Rf=0.82.
MS 437 (M+).

Example 278

As test animals, four male rats (weighing 400 to 440 g) with spontaneous hypertension that were sufficiently adapted for feeding and hypertension was confirmed were used.

Physiological saline aqueous solution containing 2.5% Nicole of sample and 2.5% ethanol was intravenously administered at once in a dose of 1 ml/kg. Blood pressure after the administration was measured by the tail-cuff method.

The results are shown below

TABLE 3

| Exp No. | Dose (mg/kg) | Reduction of Blood Pressure (mmHg) Time After Administration | |
|---|---|---|---|
| | | 0.5 hr | 4 hr |
| 111 | 10 | −109 | −67 |
| 112 | 10 | −72 | −73 |
| 113 | 10 | −135 | −80 |
| 114 | 10 | −125 | −53 |
| 115 | 10 | −61 | −31 |
| 116 | 10 | −34 | −34 |
| 117 | 10 | −62 | −31 |
| 118 | 10 | −70 | −51 |
| 119 | 10 | −78 | −72 |
| 120 | 10 | −45 | −45 |
| 121 | 10 | −85 | −72 |
| 122 | 10 | −91 | −65 |
| 123 | 10 | −100 | −71 |
| 124 | 10 | −21 | −21 |
| 125 | 10 | −25 | −5 |
| 126 | 10 | −45 | −51 |
| 127 | 10 | −51 | −37 |
| 128 | 10 | −28 | −40 |
| 129 | 10 | −55 | −20 |
| 130 | 10 | −51 | −3 |
| 131 | 10 | −41 | −21 |
| 132 | 10 | −20 | −21 |

TABLE 3-continued

| Exp No. | Dose (mg/kg) | Reduction of Blood Pressure (mmHg) Time After Administration | |
| --- | --- | --- | --- |
| | | 0.5 hr | 4 hr |
| 133 | 10 | −21 | −20 |
| 134 | 10 | −40 | −44 |
| 135 | 10 | −30 | −18 |
| 136 | 10 | −27 | −21 |
| 139 | 10 | −89 | −50 |
| 140 | 10 | −100 | −37 |
| 141 | 10 | −103 | −58 |
| 142 | 10 | −129 | −65 |
| 143 | 3 | −67 | −33 |
| 144 | 10 | −45 | −42 |
| 145 | 10 | −14 | −14 |
| 146 | 10 | −85 | −45 |
| 147 | 3 | −23 | 2 |
| 149 | 10 | −65 | −6 |
| 152 | 10 | −125 | −93 |
| 153 | 10 | −125 | −101 |
| 154 | 10 | −67 | 1 |
| 155 | 10 | −125 | −34 |
| 156 | 10 | −140 | −51 |
| 157 | 10 | −76 | 0 |
| 158 | 10 | −56 | −20 |
| 163 | 10 | −129 | −21 |
| 165 | 10 | −27 | 1 |
| 166 | 10 | −47 | 4 |
| 167 | 10 | −105 | −10 |
| 168 | 10 | −130 | −136 |
| 169 | 10 | −114 | −30 |
| 170 | 10 | −84 | −16 |
| 173 | 10 | −37 | 2 |
| 178 | 10 | −8 | −7 |
| 189 | 10 | −78 | −36 |
| 190 | 10 | −140 | −76 |
| 191 | 10 | −87 | −19 |
| 194 | 10 | −66 | −14 |
| 196 | 10 | −14 | 1 |
| 204 | 10 | −23 | −9 |
| 212 | 10 | −121 | −48 |
| 252 | 10 | −35 | −5 |
| 259 | 10 | −88 | −19 |
| 260 | 10 | −126 | −50 |
| 263 | 10 | −98 | −13 |
| 264 | 10 | −16 | 0 |
| 265 | 1 | −151 | −81 |
| 267 | 10 | −53 | −19 |
| 268 | 10 | −36 | −12 |
| 269 | 10 | −143 | −25 |
| 270 | 10 | −129 | −24 |
| 271 | 10 | −34 | −5 |
| 272 | 3 | −17 | −12 |
| 273 | 10 | −42 | −19 |
| 274 | 10 | −120 | −62 |
| 275 | 10 | −55 | −7 |
| 276 | 10 | −90 | −20 |
| 277 | 10 | −93 | −14 |

Obviously, numerous modifications and variations of the present invention are possible in light of the above teachings. It is therefore to be understood that within the scope of the appended claims, the invention may be practiced otherwise than as specifically described herein.

What is new and desired to be secured by Letters Patent of the United States is:

1. An ethylamine compound of formula (I):

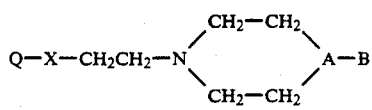

wherein the moiety A-B is selected from the group consisting of

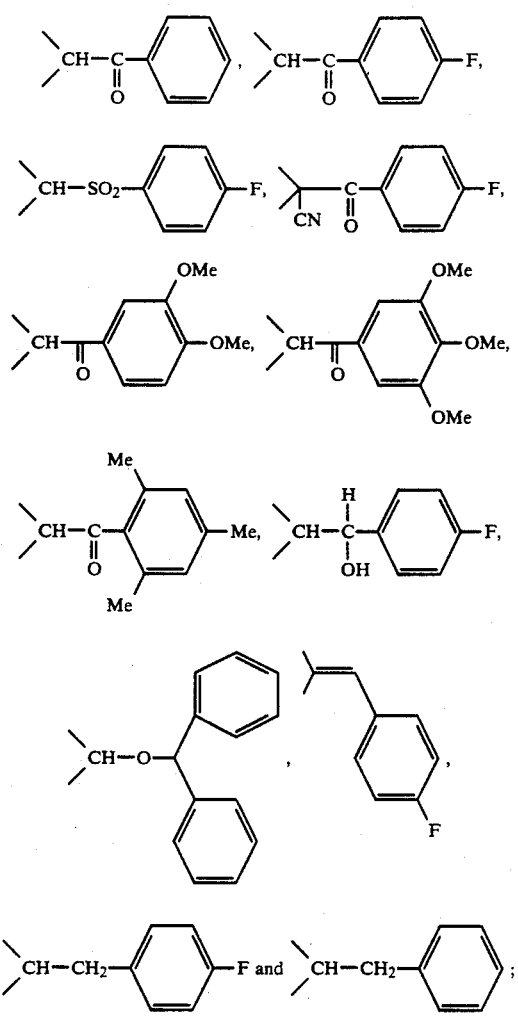

Q is a member selected from the group consisting of o-nitrophenyl, o-aminophenyl, o-ethylcarbamoylphenyl, o-styrylcarbamoylphenyl, 1-naphthyl, 2-naphthyl, 3,4-dimethoxyphenyl, 3,4,5-trimethoxyphenyl, 3,4-dichlorophenyl, 3-methoxyphenyl, 3,4-dihydroxyphenyl, 3-trifluoromethylphenyl, pyrrolyl, N-methylpyrrolyl, 4-methoxyphenyl, 3-benzoylphenyl, phenyl, 3,4-dimethylphenyl, 2-methoxy-5-bromophenyl, 2-fluorophenyl, 3-fluorophenyl, 3-fluoro-4-methoxyphenyl, 3-chlorophenyl, 3-iodophenyl, 3-phenoxyphenyl, 3-methoxy-4-benzyloxyphenyl, 3,5-dimethoxyphenyl, 3-benzyloxphenyl, 3,4-dibenzyloxyphenyl, 3-ethoxy-4-methoxyphenyl, 3-ethoxyphenyl, 2-methylnaphthyl, 2-bromophenyl, 2-bromo-4,5-dimethoxyphenyl, pentafluorophenyl, 2-chlorophenyl, 2,3,6-trichlorophenyl, 2,4-dichlorophenyl, 2-chloro-6-fluorophenyl, 2,6-dichlorophenyl, 2,6-dimethylphenyl, 2-iodophenyl, 2-nitro-4-trifluoromethylphenyl, 2-phenoxyphenyl, 2-methoxyphenyl, 2,3-dimethoxyphenyl, 2,3,4-trimethoxyphenyl, 2,4,5-trimethoxyphenyl, 2,5-dimethoxyphenyl, 2-benzyloxyphenyl, 2-ethoxyphenyl, o-biphenyl, 2-trifluorophenyl, 2-methylphenyl, 2,3-dimethyl-4-methoxyphenyl, 3-methylphenyl, 3-methyl-4-methoxyphenyl, 3,4-dimethylphenyl, 3,4,5-trimethylphenyl, 4-cyanophenyl, 4- bromophenyl, 4-fluorophenyl, 4-chlorophenyl, 4-iodophenyl, 4-phenoxyphenyl, 4-benzyloxyphenyl, 4-ethoxyphenyl, 3-methoxy-4-ethoxyphenyl, 4-(2-diethylaminoethoxy)phenyl, 3-methoxy-4-hydroxy-5-bromophenyl, 3-methoxy-4-hydroxyphenyl, 3,5-dimethoxy-4-hydroxyphenyl, 3-ethoxy-4-hydroxyphenyl, p-biphenyl, 4-butoxyphenyl, 4-(2'-methyl-2'-butyl)phenyl, 4-isopropylphenyl, p-tolyl, 4-benzylphenyl, 4-ethylphenyl, 4-hydroxyphenyl, 2-cyano-4-methylphenyl, 3,4-methylenedioxyphenyl, 3-pyridyl, 2-nitrophenyl, 2-chloro-4-nitrophenyl, 3-nitrophenyl, 2-nitro-5-fluorophenyl, 4-nitrophenyl, 4-aminophenyl, 3,5-di(trifluoromethyl)phenyl, 2,4-difluorophenyl, 2,5-difluorophenyl, 2,6-difluorophenyl, 3,4-difluorophenyl, 2,4-di(trifluoromethyl)phenyl, 3,5-difluorophenyl, 4-ethenylphenyl, 2,4,5-trimethylphenyl, 2-hydroxy-3-methoxyphenyl, 2-hydroxy-3-ethoxyphenyl, 4-(2'-methylpropyl)phenyl, 4-methoxycarbonylphenyl, 3,4-diethoxyphenyl, 2-iodo-4,5-dimethoxyphenyl, 4-neopentanoylphenyl, 2-nitro-4,5-dimethoxyphenyl, 2-thiopheno, 2-furyl, 3-pyrrolyl, N-methyl-3-pyrrolyl, 3-thiopheno, 3-furyl, n-butyl, cyclohexyl, 3-(α-hydroxybenzyl)-phenyl, 4-trifluoromethylphenyl and 3-methoxyphenyl;

X is a member selected from the group consisting of $$\begin{array}{c} R \\ | \\ -C-(CH_2)_n- \\ | \\ R_1 \end{array}$$

—CO—(CH$_2$)$_m$—, —CHOH—(CH$_2$)$_o$—, —S(O)$_k$—(CH$_2$)$_l$—, —(CH$_2$)$_p$—, —O—(CH$_2$)$_q$—, —SO$_2$—NH—, —CO—NH—, —NH—CO—NH—,

[dioxolane and disulfone cyclic structures with (CH$_2$)$_r$ and (CH$_2$)$_s$ substituents]

wherein
R is hydrogen, C$_{1-15}$ alkyl, C$_{3-8}$ cycloalkyl, 3-chloropropyl, phenyl, benzyl, phenylthio, 1-naphthyl or 2-naphthyl,
R$^1$ is —CN, —CONH$_2$, —COOCH$_3$,
n is an integer of from 0 to 6,
m is an integer of from 0 to 6,
o is an integer of from 0 to 6,
p is an integer of from 0 to 12,
k is an integer of from 0 to 2,
l is an integer of from 2 to 4,
q is an integer of from 2 to 4,
r is an integer of from 2 to 4, and
s is an integer of from 2 to 4; or
a physiologically acceptable salt thereof.

2. The ethylamine compound of claim 1, wherein A-B is:

[two structural formulas shown]

3. The ethylamine compound of claim 1, having a formula selected from the group consisting of:

[series of chemical structures]

-continued

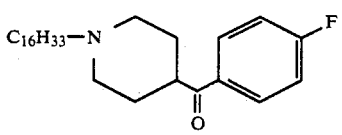

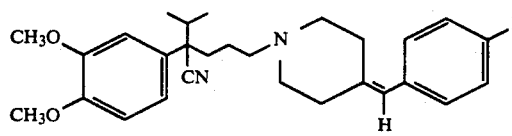

4. The ethylamine compound of claim 2; wherein X is

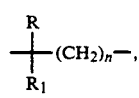

—CO—(CH₂)ₘ—, —S(O)ₖ—(CH₂)ₗ—, —(CH₂)ₚ—,
—SO₂—NH— and

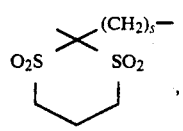

wherein
R is hydrogen, C₁₋₁₅ alkyl, C₃₋₈ cycloalkyl, 3-chloropropyl, phenyl, benzyl, phenylthio, 1-naphthyl or 2-naphthyl,
R¹ is —CN, —CONH₂ or —COOCH₃,
n is an integer of from 0 to 6,
m is an integer of from 0 to 6,
p is an integer of from 0 to 12,
k is an integer of from 0 to 2,
l is an integer of from 2 to 4, and
s is an integer of from 2 to 4.

5. The ethylamine compound of claim 4, having a formula selected from the group consisting of:

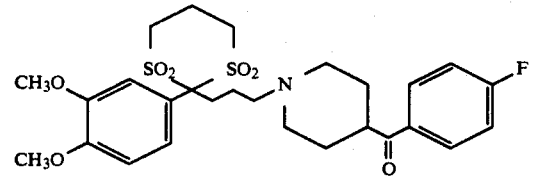

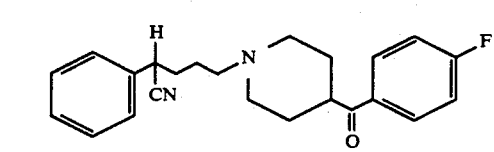

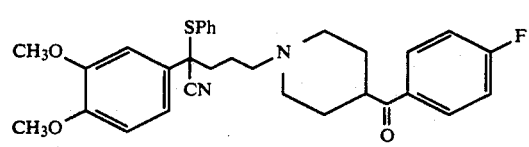

-continued

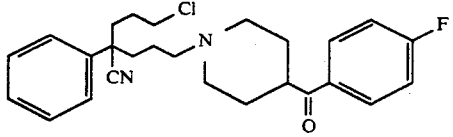

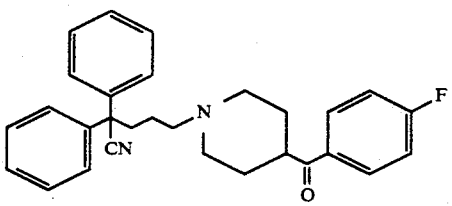

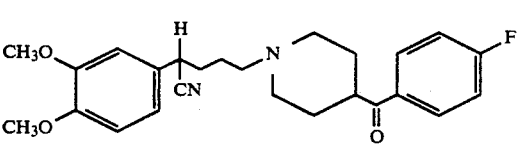

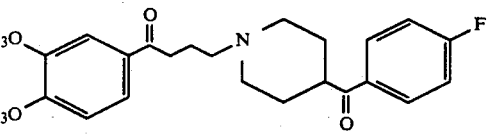

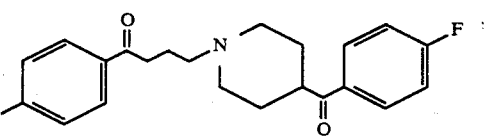

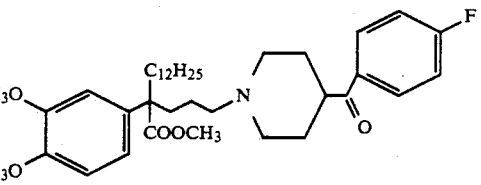

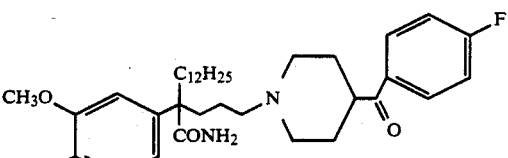

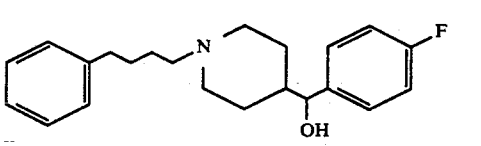

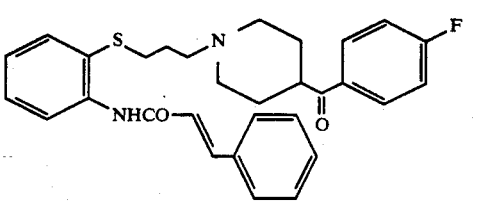

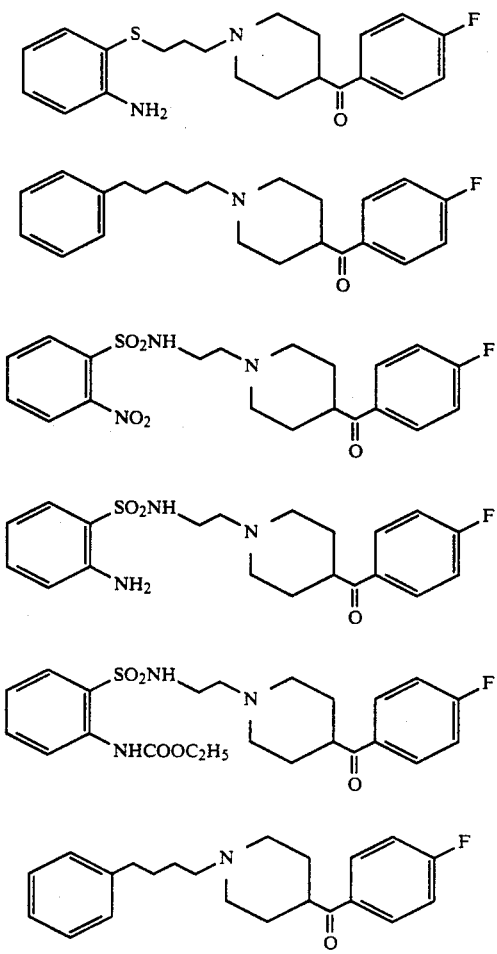
6. The ethylamine compound of claim 2, wherein X is
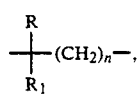
R is $C_{1-15}$ alkyl or $C_{3-8}$ cycloalkyl, $R^1$ is —CN, and n is an integer of from 0 to 6.
7. The ethylamine compound of claim 4, having a formula selected from the group consisting of:
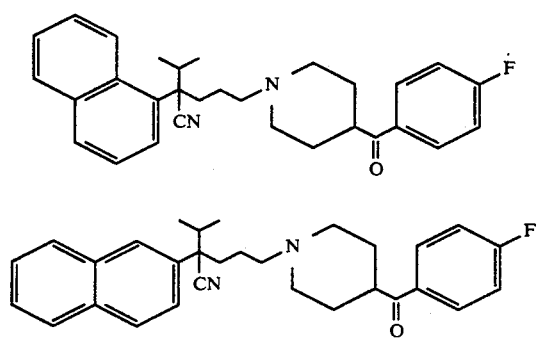
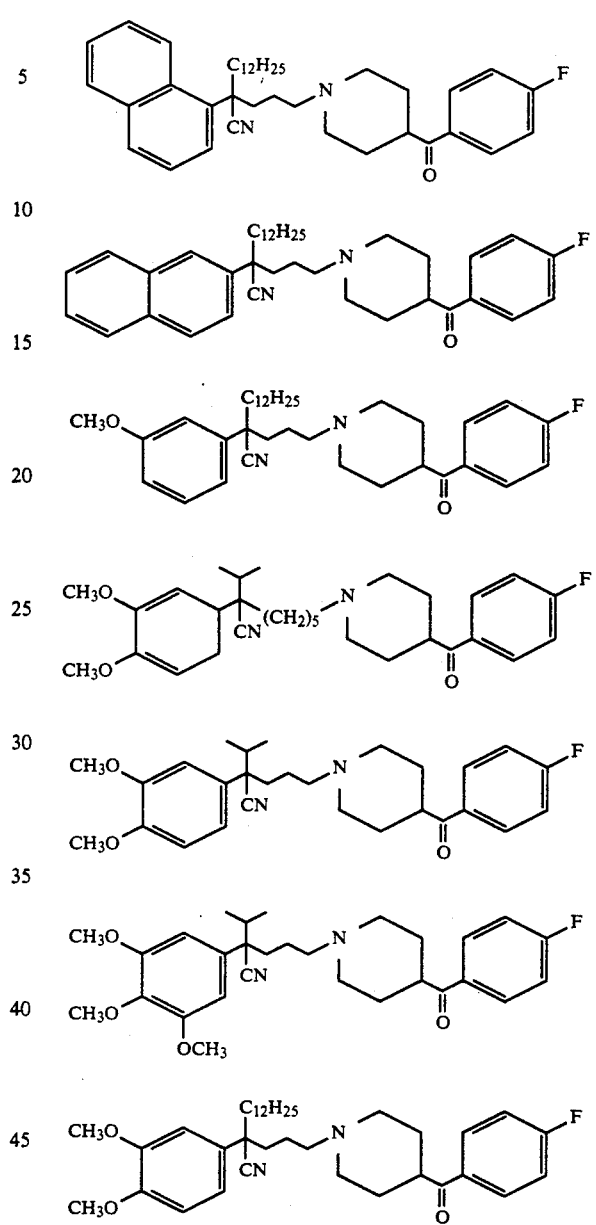
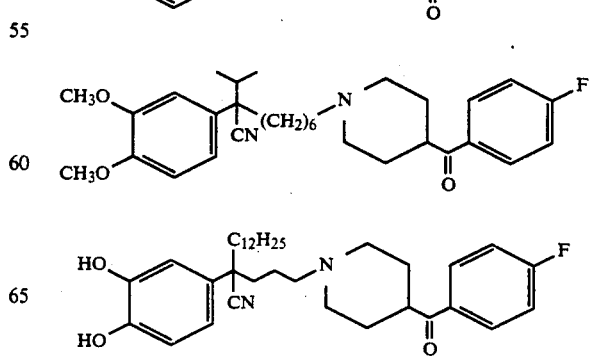

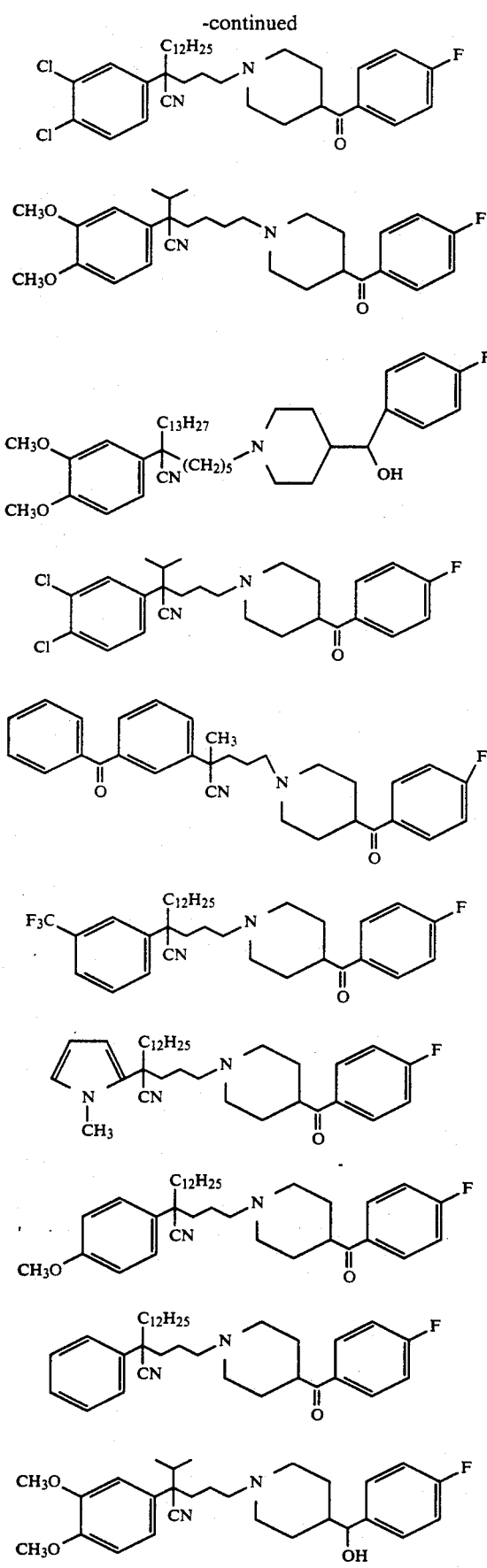
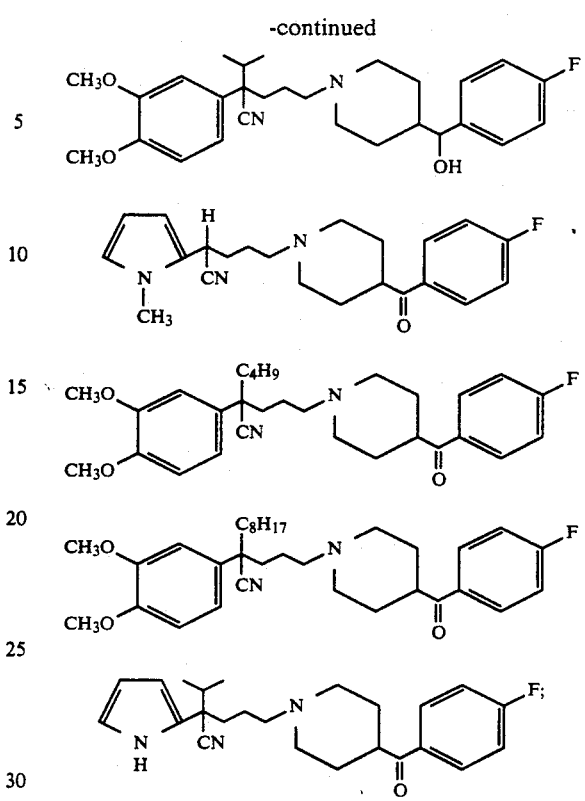
compounds of the formula:
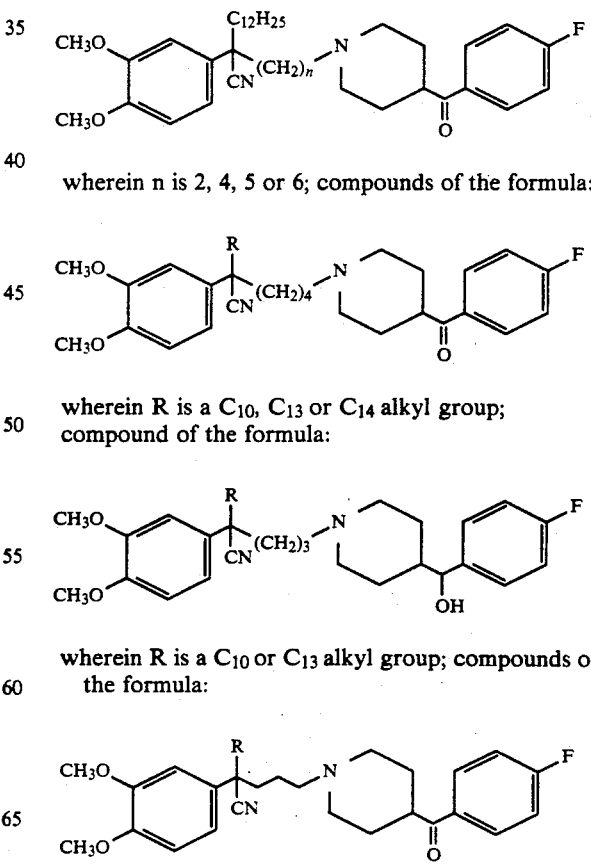
wherein n is 2, 4, 5 or 6; compounds of the formula:
[structure with R and (CH2)4]
wherein R is a C10, C13 or C14 alkyl group;
compound of the formula:
[structure with R and (CH2)3 and OH]
wherein R is a C10 or C13 alkyl group; compounds of the formula:
[structure with R]

wherein R is $C_{1-7}$ alkyl, $C_{9-15}$ alkyl, $C_{3-6}$ cycloalkyl, $C_8$ cycloalkyl, phenyl, benzyl, 1-naphthyl or 2-naphthyl;

compounds of the formula:

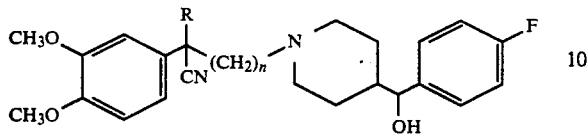

wherein n is 3 and R is $C_{1-11}$ alkyl or $C_{14}$ alkyl; or R is $C_{12}$ alkyl and n is 2, 4, 5 or 6; and compounds of the formula:

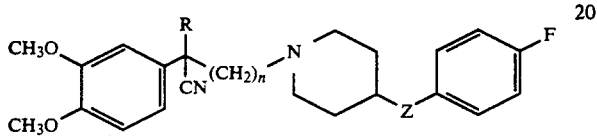

wherein Z is —(CHOH)—, n is 4–6 and R is $C_{10-11}$ alkyl or $C_{13-14}$ alkyl; Z is —(C=O)—, n is 4–6 and R is $C_{10-11}$ alkyl or $C_{13-14}$ alkyl; and Z is —(C=O)—, n is 2 and R is $C_{10}$ alkyl or $C_{12}$ alkyl.

8. An ethylamine compound of formula (I):

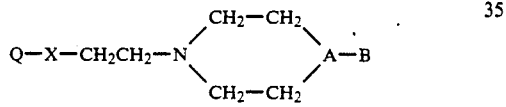

wherein the moiety of A-B is selected from the group consisting of

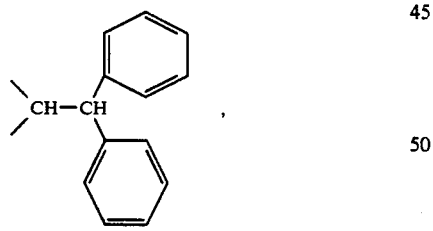,

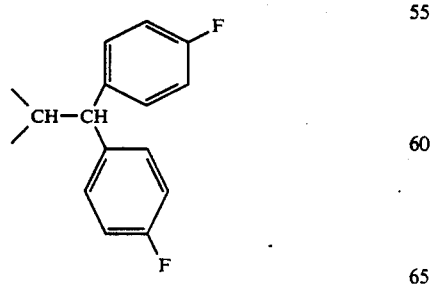

and

-continued

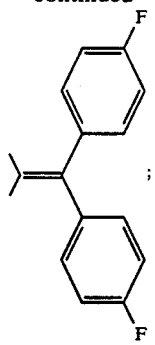;

Q is a member selected from the group consisting of o-nitrophenyl, o-aminophenyl, o-ethylcarbamoylphenyl, o-styrylcarbamoylphenyl, 1-naphthyl, 2-naphthyl, 3,4-dimethoxyphenyl, 3,4,5-trimethoxyphenyl, 3,4-dichlorophenyl, 3-methoxyphenyl, 3,4-dihydroxyphenyl, 3-trifluoromethylphenyl, pyrrolyl, N-methylpyrrolyl, 4-methoxyphenyl, 3-benzoylphenyl, phenyl, 3,4-dimethylphenyl, 2-methoxy-5-bromophenyl, 2-fluorophenyl, 3-fluorophenyl, 3-fluoro-4-methoxyphenyl, 3-chlorophenyl, 3-iodophenyl, 3-phenoxyphenyl, 3-methoxy-4-benzyloxyphenyl, 3,5-dimethoxyphenyl, 3-benzyloxphenyl, 3,4-dibenzyloxyphenyl, 3-ethoxy-4-methoxyphenyl, 3-ethoxyphenyl, 2-methylnaphthyl, 2-bromophenyl, 2-bromo-4,5-dimethoxyphenyl, pentafluorophenyl, 2-chlorophenyl, 2,3,6-trichlorophenyl, 2,4-dichlorophenyl, 2-chloro-6-fluorophenyl, 2,6-dichlorophenyl, 2,6-dimethylphenyl, 2-iodophenyl, 2-nitro-4-trifluoromethylphenyl, 2-phenoxyphenyl, 2-methoxyphenyl, 2,3-dimethoxyphenyl, 2,3,4-trimethoxyphenyl, 2,4,5-trimethoxyphenyl, 2,5-dimethoxyphenyl, 2-benzyloxyphenyl, 2-ethoxyphenyl, o-biphenyl, 2-trifluorophenyl, 2-methylphenyl, 2,3-dimethyl-4-methoxyphenyl, 3-methylphenyl, 3-methyl-4-methoxyphenyl, 3,4-dimethylphenyl, 3,4,5-trimethylphenyl, 4-cyanophenyl, 4-bromophenyl, 4-fluorophenyl, 4-chlorophenyl, 4-iodophenyl, 4-phenoxyphenyl, 4-benzyloxyphenyl, 4-ethoxyphenyl, 3-methoxy-4-ethoxyphenyl, 4-(2-diethylaminoethoxy)phenyl, 3-methoxy-4-hydroxy-5-bromophenyl, 3-methoxy-4-hydroxyphenyl, 3,5-dimethoxy-4-hydroxyphenyl, 3-ethoxy-4-hydroxyphenyl, p-biphenyl, 4-butoxyphenyl, 4-(2'-methyl-2'-butyl)phenyl, 4-isopropylphenyl, p-tolyl, 4-benzylphenyl, 4-ethylphenyl, 4-hydroxyphenyl, 2-cyano-4-methylphenyl, 3,4-methylenedioxyphenyl, 3-pyridyl, 2-nitrophenyl, 2-chloro-4-nitrophenyl, 3-nitrophenyl, 2-nitro-5-fluorophenyl, 4-nitrophenyl, 4-aminophenyl, 3,5-di(trifluoromethyl)phenyl, 2,4-difluorophenyl, 2,5-difluorophenyl, 2,6-difluorophenyl, 3,4-difluorophenyl, 2,4-di(trifluoromethyl)phenyl, 3,5-difluorophenyl, 4-ethenylphenyl, 2,4,5-trimethylphenyl, 2-hydroxy-3-methoxyphenyl, 2-hydroxy-3-ethoxyphenyl, 4-(2'-methylpropyl)phenyl, 4-methoxycarbonylphenyl, 3,4-diethoxyphenyl, 2-iodo-4,5-dimethoxyphenyl, 4-neopentanoylphenyl, 2-nitro-4,5-dimethoxyphenyl, 2-thiopheno, 2-furyl, 3-pyrrolyl, N-methyl-3-pyrrolyl, 3-thiopheno, 3-furyl, cyclohexyl, 3-(α-hydroxybenzyl)phenyl, 4-trifluoromethylphenyl and 3-methoxyphenyl;

X is a member selected from the group consisting of $$\underset{R_1}{\overset{R}{+}}(CH_2)_n—,$$

—S(O)$_k$—(CH$_2$)$_l$—, —O—(CH$_2$)$_q$—, —SO$_2$—NH—, —CO—NH—, —NH—CO—NH—,

[1,3-dioxolane with (CH$_2$)$_r$—] and [cyclic sulfone with (CH$_2$)$_s$—], wherein R is hydrogen, C$_{1-15}$ alkyl, C$_{3-8}$ cycloalkyl, 3-chloropropyl, phenyl, benzyl, phenylthio, 1-naphthyl or 2-naphthyl, R$^1$ is —CN, —CONH$_2$, —COOCH$_3$, n is an integer of from 0 to 6, k is an integer of from 0 to 2, l is an integer of from 2 to 4, q is an integer of from 2 to 4, r is an integer of from 2 to 4, and s is an integer of from 2 to 4; or a physiologically acceptable salt thereof.

9. The ethylamine compound of claim 8, having a formula selected from the group consisting of:

[Structure: 3,4-dimethoxyphenyl with C$_{12}$H$_{25}$ and CN substituents, connected via CH$_2$CH$_2$ to piperidine-N, with piperidine-4-ylidene bis(4-fluorophenyl)methylene]

[Structure: 3,4-dimethoxyphenyl with isopropyl and CN substituents, connected via CH$_2$CH$_2$ to piperidine-N, with piperidine-4-ylidene bis(4-fluorophenyl)methylene]

[Structure: 3-methoxyphenyl with H and CN substituents, connected via CH$_2$CH$_2$ to piperidine-N, with piperidine-4-ylidene bis(4-fluorophenyl)methylene]

10. An ethylamine compound of formula (I):

$$Q—X—CH_2CH_2—N\underset{CH_2—CH_2}{\overset{CH_2—CH_2}{\diagup\diagdown}}A—B$$

wherein the moiety A-B is

[dibenzocycloheptylidene structure]

Q is a member selected from the group consisting of o-nitrophenyl, o-aminophenyl, o-ethylcarbamoylphenyl, o-styrylcarbamoylphenyl, 1-naphthyl, 2-naphthyl, 3,4-dimethoxyphenyl, 3,4,5-trimethoxyphenyl, 3,4-dichlorophenyl, 3-methoxyphenyl, 3,4-dihydroxyphenyl, 3-trifluoromethylphenyl, pyrrolyl, N-methylpyrrolyl, 4-methoxyphenyl, 3-benzoylphenyl, phenyl, 3,4-dimethylphenyl, 2-methoxy-5-bromophenyl, 2-fluorophenyl, 3-fluorophenyl, 3-fluoro-4-methoxyphenyl, 3-chlorophenyl, 3-iodophenyl, 3-phenoxyphenyl, 3-methoxy-4-benzyloxyphenyl, 3,5-dimethoxyphenyl, 3-benzyloxphenyl, 3,4-dibenzyloxyphenyl, 3-ethoxy-4-methoxyphenyl, 3-ethoxyphenyl, 2-methylnaphthyl, 2-bromophenyl, 2-bromo-4,5-dimethoxyphenyl, pentafluorophenyl, 2-chlorophenyl, 2,3,6-trichlorophenyl, 2,4-dichlorophenyl, 2-chloro-6-fluorophenyl, 2,6-dichlorophenyl, 2,6-dimethylphenyl, 2-iodophenyl, 2-nitro-4-trifluoromethylphenyl, 2-phenoxyphenyl, 2-methoxyphenyl, 2,3-dimethoxyphenyl, 2,3,4-trimethoxyphenyl, 2,4,5-trimethoxyphenyl, 2,5-dimethoxyphenyl, 2-benzyloxyphenyl, 2-ethoxyphenyl, o-biphenyl, 2-trifluorophenyl, 2-methylphenyl, 2,3-dimethyl-4-methoxyphenyl, 3-methylphenyl, 3-methyl-4-methoxyphenyl, 3,4-dimethylphenyl, 3,4,5-trimethylphenyl, 4-cyanophenyl, 4-bromophenyl, 4-fluorophenyl, 4-chlorophenyl, 4-iodophenyl, 4-phenoxyphenyl, 4-benzyloxyphenyl, 4-ethoxyphenyl, 3-methoxy-4-ethoxyphenyl, 4-(2-diethylaminoethoxy)phenyl, 3-methoxy-4-hydroxy-5-bromophenyl, 3-methoxy-4-hydroxyphenyl, 3,5-dimethoxy-4-hydroxyphenyl, 3-ethoxy-4-hydroxyphenyl, p-biphenyl, 4-butoxyphenyl, 4-(2'-methyl-2'-butyl)phenyl, 4-isopropylphenyl, p-tolyl, 4-benzylphenyl, 4-ethylphenyl, 4-hydroxyphenyl, 2-cyano-4-methylphenyl, 3,4-methylenedioxyphenyl, 3-pyridyl, 2-nitrophenyl, 2-chloro-4-nitrophenyl, 3-nitrophenyl, 2-nitro-5-fluorophenyl, 4-nitrophenyl, 4-aminophenyl, 3,5-di(trifluoromethyl)phenyl, 2,4-difluorophenyl, 2,5-difluorophenyl, 2,6-difluorophenyl, 3,4-difluorophenyl, 2,4-di(trifluoromethyl)phenyl, 3,5-difluorophenyl, 4-ethenylphenyl, 2,4,5-trimethylphenyl, 2-hydroxy-3-methoxyphenyl, 2-hydroxy-3-ethoxyphenyl, 4-(2'-methylpropyl)phenyl, 4-methoxycarbonylphenyl, 3,4-diethoxyphenyl, 2- iodo-4,5-dimethoxyphenyl, 4-neopentanoylphenyl, 2-nitro-4,5-dimethoxyphenyl, 2-thiopheno, 2-furyl, 3-pyrrolyl, N-methyl-3-pyrrolyl, 3-thiopheno, 3-furyl, cyclohexyl, 3-(α-hydroxybenzyl)phenyl, 4-trifluoromethylphenyl and 3-methoxyphenyl;

X is a member selected from the group consisting of

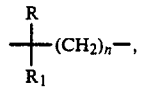

—S(O)$_k$—(CH$_2$)$_l$—,  —SO$_2$—NH—,
—CO—NH—, —NH—CO—NH—,

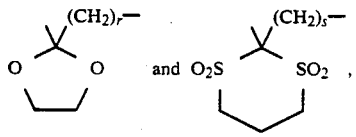

wherein

R is hydrogen, C$_{1-15}$ alkyl, C$_{3-8}$ cycloalkyl, 3-chloropropyl, phenyl, benzyl, phenylthio, 1-naphthyl or 2-naphthyl, R$^1$ is —CN, —CONH$_2$, —COOCH$_3$, n is an integer of from 0 to 6, k is an integer of from 0 to 2, l is an integer of from 2 to 4, r is an integer of from 2 to 4, and s is an integer of from 2 to 4; or a physiologically acceptable salt thereof.

11. The ethylamine compound of claim 10, wherein Q is a member selected from the group consisting of o-nitrophenyl, o-aminophenyl, o-ethylcarbamoylphenyl, o-styrylcarbamoylphenyl, 1-naphthyl, 2-naphthyl, 3,4-dimethoxyphenyl, 3,4,5-trimethoxyphenyl, 3,4-dichlorophenyl, 3-methoxyphenyl, 3,4-dihydroxyphenyl, 3-trifluoromethylphenyl, pyrrolyl, N-methylpyrrolyl, 4-methoxyphenyl, 3-benzoylphenyl, phenyl, 3,4-dimethylphenyl, 2-methoxy-5-bromophenyl, 2-fluorophenyl, 3-fluorophenyl, 3-fluoro-4-methoxyphenyl, 3-chlorophenyl, 3-iodophenyl, 3-phenoxyphenyl, 3-methoxy-4-benzyloxyphenyl, 3,5-dimethoxyphenyl, 3-benzyloxphenyl, 3,4-dibenzyloxyphenyl, 3-ethoxy-4-methoxyphenyl, 3-ethoxyphenyl, 2-methylnaphthyl, 2-bromophenyl, 2-bromo-4,5-dimethoxyphenyl, pentafluorophenyl, 2-chlorophenyl, 2,3,6-trichlorophenyl, 2,4-dichlorophenyl, 2-chloro-6-fluorophenyl, 2,6-dichlorophenyl, 2,6-dimethylphenyl, 2-iodophenyl, 2-nitro-4-trifluoromethylphenyl, 2-phenoxyphenyl, 2-methoxyphenyl, 2,3-dimethoxyphenyl, 2,3,4-trimethoxyphenyl, 2,4,5-trimethoxyphenyl, 2,5-dimethoxyphenyl, 2-benzyloxyphenyl, 2-ethoxyphenyl, o-biphenyl, 2-trifluorophenyl, 2-methylphenyl, 2,3-dimethyl-4-methoxyphenyl, 3-methylphenyl, 3-methyl-4-methoxyphenyl, 3,4-dimethylphenyl, 3,4,5-trimethoxyphenyl, 4-cyanophenyl, 4-bromophenyl, 4-fluorophenyl, 4-chlorophenyl, 4-iodophenyl, 4-phenoxyphenyl, 4-benzyloxyphenyl, 4-ethoxyphenyl, 3-methoxy-4-ethoxyphenyl, 4-(2-diethylaminoethoxy)phenyl, 3-methoxy-4-hydroxy-5-bromophenyl, 3-methoxy-4-hydroxyphenyl, 3,5-dimethoxy-4-hydroxyphenyl, 3-ethoxy-4-hydroxyphenyl, p-biphenyl, 4-butoxyphenyl, 4-benzylphenyl, 4-hydroxyphenyl, 2-cyano-4-methylphenyl, 3,4-methylenedioxyphenyl, 3-pyridyl, 2-nitrophenyl, 2-chloro-4-nitrophenyl, 3-nitrophenyl, 2-nitro-5-fluorophenyl, 4-nitrophenyl, 4-aminophenyl, 3,5-di(trifluoromethyl)phenyl, 2,4-difluorophenyl, 2,5-difluorophenyl, 2,6-difluorophenyl, 3,4-difluorophenyl, 2,4-di(trifluoromethyl)phenyl, 3,5-difluorophenyl, 4-ethenylphenyl, 2,4,5-trimethylphenyl, 2-hydroxy-3-methoxyphenyl, 2-hydroxy-3-ethoxyphenyl, 4-methoxycarbonylphenyl, 3,4-diethoxyphenyl, 2-iodo-4,5-dimethoxyphenyl, 4-neopentanoylphenyl, 2-nitro-4,5-dimethoxyphenyl, 2-thiopheno, 2-furyl, 3-pyrrolyl, N-methyl-3-pyrrolyl, 3-thiopheno, 3-furyl, cyclohexyl, 3-(α-hydroxybenzyl)phenyl, 4-trifluoromethylphenyl and 3-methoxyphenyl.

12. The ethylamine compound of claim 11, having a formula selected from the group consisting of:

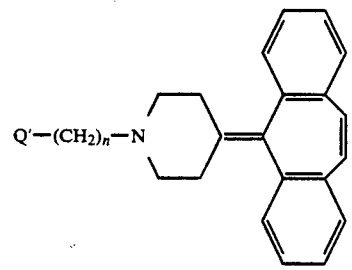

wherein Q' is CH$_3$ and n is 7, 9, 11, 13 or 15; Q' is cyclohexyl and n is 2–5; Q' is phenyl and n is 2–7; Q' is phenoxy and n is 2–4; Q' is phenylthio and n is 2–4; n is 2 and Q' is 3',4'-dimethoxyphenyl,

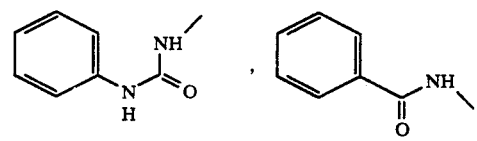

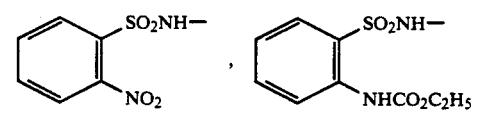

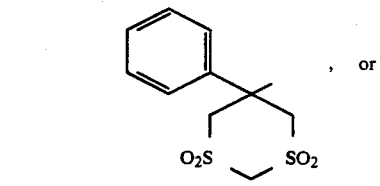

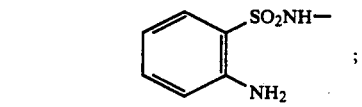

or n is 3 and Q' is 4'-fluorophenylsulfoxyl, 4'-fluorophenylsulfonyl, 2'-aminophenylthio, or a substituent selected from the following:

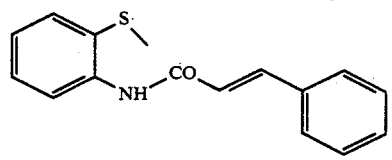

-continued
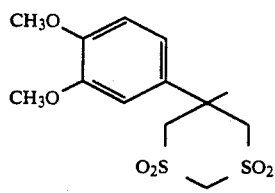
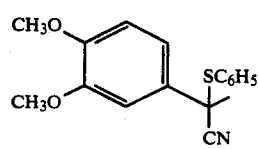
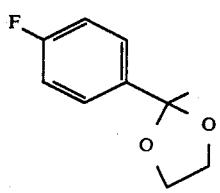
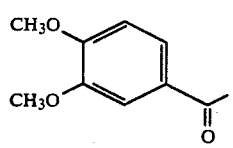
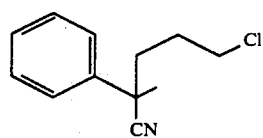
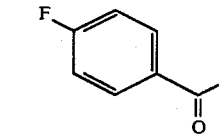
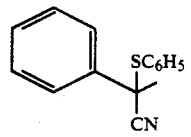
13. The ethylamine compound of claim 11, wherein X is a member selected from the group consisting of
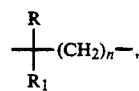
—SO$_2$—NH—, —CO—NH—, —NH—CO—NH—,
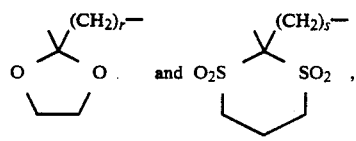
14. The ethylamine compound of claim 13, wherein X is
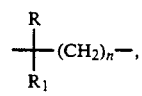
R is hydrogen or C$_{1-15}$ alkyl, and R$^1$ is —CN.
15. The ethylamine compound of claim 14, having a formula selected from the group consisting of:
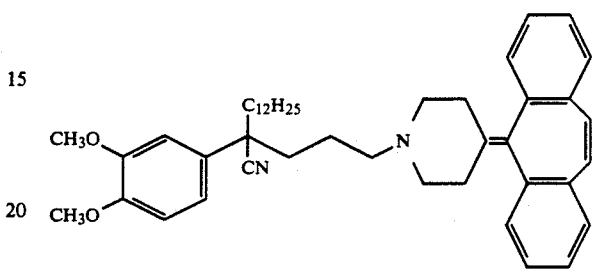
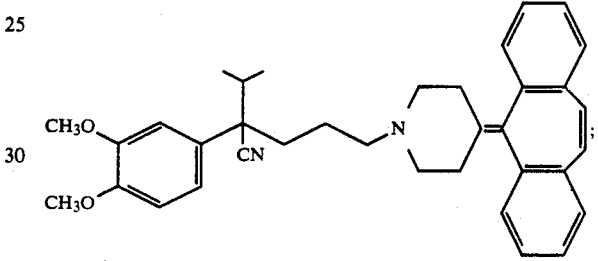
the formula:
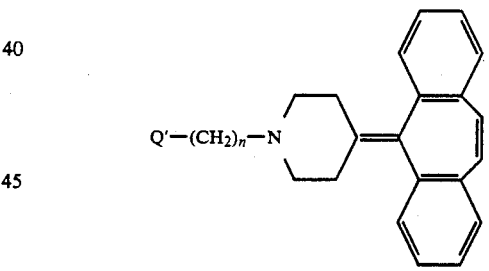
wherein n is 3 and Q' is selected from the following:
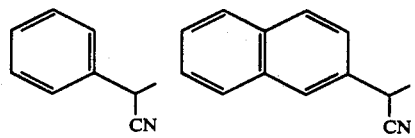
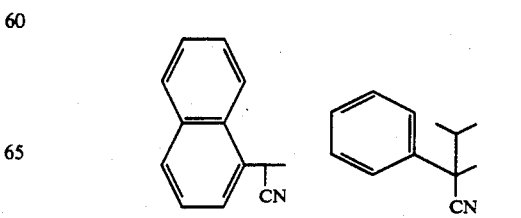

-continued
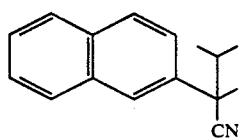
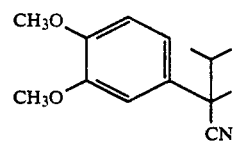
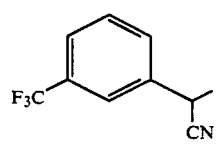
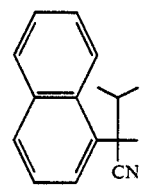
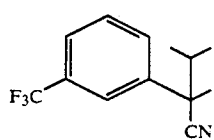
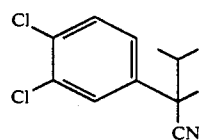
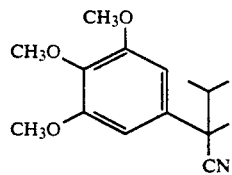
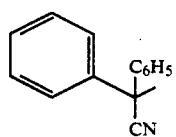
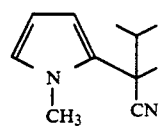
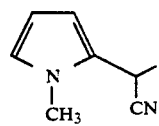
-continued
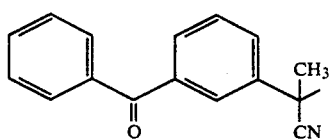
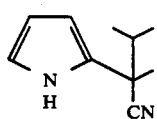
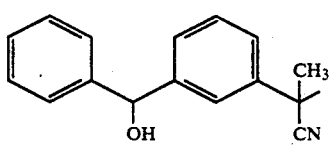
n is 4 and Q' is selected from the following:
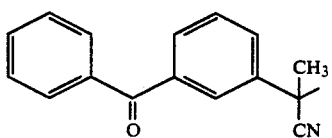
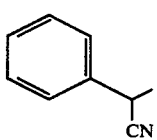
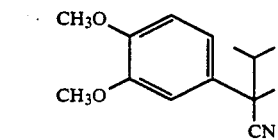
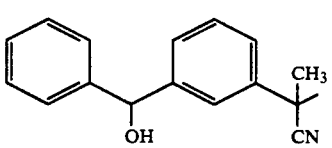
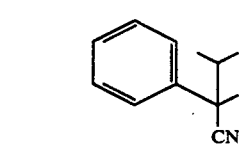
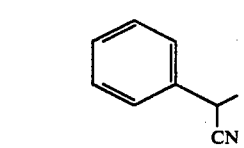
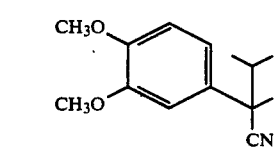

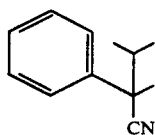

n is 5 and Q' is selected from the following:

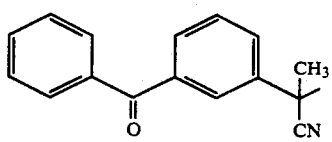

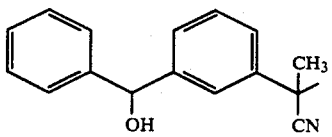

n is 6 and Q' is selected from the following:

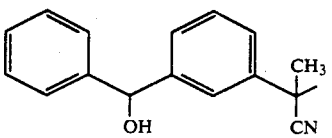

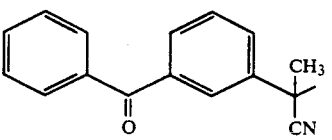

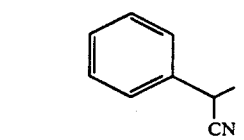

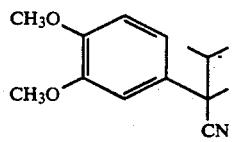

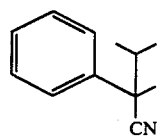

and the formula:

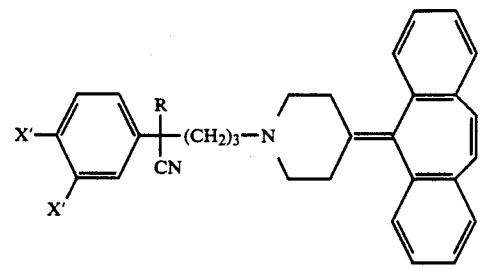

wherein X' is hydrogen or methoxy, and R is $C_{1-10}$ alkyl.

16. The compound of formula (I) as claimed in claim 1, which is in the form of a physiologically acceptable salt.

17. 1-Cyclohexyl-4-(4-(5H-dibenzo[a,d]cyclohepten-5-ylidene)-1-piperidinyl)-butane or a physiologically acceptable salt thereof.

18. An antihypertensive composition, comprising an amount of the ethylamine compound of claim 1 effective to treat hypertension and a pharmaceutically acceptable excipient.

19. The composition of claim 18, further comprising a member selected from the group consisting of a diuretic, a calcium antagonist, a β-blocker, an α-blocker and a converting enzyme inhibitor.

20. An antihypertensive composition, comprising an amount of the ethylamine compound of claim 8 effective to treat hypertension and a pharmaceutically acceptable excipient.

21. The composition of claim 20, further comprising a member selected from the group consisting of a diuretic, a calcium antagonist, a β-blocker, an α-blocker and a converting enzyme inhibitor.

22. An antihypertensive composition, comprising an amount of the ethylamine compound of claim 10 effective to treat hypertension and a pharmaceutically acceptable excipient.

23. The composition of claim 22, further comprising a member selected from the group consisting of a diuretic, a calcium antagonist, a β-blocker, an α-blocker and a converting enzyme inhibitor.

* * * * *

UNITED STATES PATENT AND TRADEMARK OFFICE
CERTIFICATE OF CORRECTION

PATENT NO. : 5,231,105
DATED : July 27, 1993
INVENTOR(S) : Masataka Shoji et al.

It is certified that error appears in the above-indentified patent and that said Letters Patent is hereby corrected as shown below:

On the title page, Item [75],

The fifth inventor's first name is spelled incorrectly, should read:

--Yoshikatsu--

Signed and Sealed this

Twelfth Day of April, 1994

Attest:

BRUCE LEHMAN

Attesting Officer

Commissioner of Patents and Trademarks